(12) United States Patent
Yang et al.

(10) Patent No.: US 7,058,650 B2
(45) Date of Patent: Jun. 6, 2006

(54) METHODS FOR ESTABLISHING A PATHWAYS DATABASE AND PERFORMING PATHWAY SEARCHES

(76) Inventors: Yonghong Yang, 4230 Ranwick Ct., San Jose, CA (US); John Tillinghast, 10684 Carver Dr., Cupertino, CA (US); Christopher Piercy, 19503 Howard Ct., Cupertino, CA (US)

( * ) Notice: Subject to any disclaimer, the term of this patent is extended or adjusted under 35 U.S.C. 154(b) by 516 days.

(21) Appl. No.: 10/081,904

(22) Filed: Feb. 20, 2002

(65) Prior Publication Data

US 2003/0100996 A1    May 29, 2003

Related U.S. Application Data

(60) Provisional application No. 60/347,019, filed on Jan. 7, 2002, provisional application No. 60/269,711, filed on Feb. 20, 2001.

(51) Int. Cl.
*G06F 7/00* (2006.01)
*G01N 33/48* (2006.01)
*C12Q 1/68* (2006.01)
*G06G 7/48* (2006.01)

(52) U.S. Cl. ............ 707/102; 707/1; 702/19; 702/20; 703/11; 435/6; 435/7.1; 530/300; 530/350

(58) Field of Classification Search ........ 707/102, 707/1; 702/19–20; 703/11; 435/6, 7.1; 530/300, 350
See application file for complete search history.

(56) References Cited

U.S. PATENT DOCUMENTS

| | | | |
|---|---|---|---|
| 6,023,659 A * | 2/2000 | Seilhamer et al. ........... | 702/19 |
| 6,643,634 B1 * | 11/2003 | Koleszar et al. ............. | 707/1 |
| 2002/0168664 A1 * | 11/2002 | Murray et al. ............... | 435/6 |
| 2002/0194201 A1 * | 12/2002 | Wilbanks et al. ......... | 707/104.1 |
| 2003/0009295 A1 * | 1/2003 | Markowitz et al. ......... | 702/20 |
| 2003/0033126 A1 * | 2/2003 | Lincoln et al. ............. | 703/11 |

OTHER PUBLICATIONS

Glavas et al (2001) T Cell Activation Up-Regulates Cyclic Nucleotide Phosphodiesterases 8A1 and 7A3. Proc Natl Acad Sci 98:6319-6324.

Altschul et al (1997) Gapped BLAST and PSI-BLAST: a new generation of protein database search programs. Nucleic Acids Res 25:3389-3402.

Pearson and Lipman (1988) Improved tools for biological sequence comparison. Proc Natl Acad Sci 85:2444-2488.

Nielsen et al (1999) Machine learning approaches for the prediction of signal peptides and other protein sorting signals. Protein Engineering 12:3-9.

Kanehisa and Goto (2000) KEGG: Kyoto Encyclopedia of Genes and Genomes. Nucleic Acids Res 28:27-30.

Nakao et al (1999) Genome-scale Gene Expression Analysis and Pathway Reconstruction in KEGG. Genome Inform Ser Workshop Genome Inform 10:94-103.

Smith and Waterman (1981) Indentification of common molecular subsequences. J Mol Biol 147:195-197.

Henikoff and Henikoff (1991) Automated assembly of protein blocks for database searching. Nucleic Acids Res 19:6565-6572.

Attwood et al (2002) Print and Print-S shed light on protein ancestry. Nucleic Acids Res 30:239-241.

Hofmann et al. (1999) The PROSITE database, its status in 1999. Nucleic Acids Res 27:215-219.

Apweiler et al (2001) The InterPro database, and integrated documentation resource for protein families, domains and functional sites. Nucleic Acids Res 29:37-40.

Schuler (1997) Pieces of the puzzle: expressed sequence tags and the catalog of human genes. J Mol Med 75:694-698.

Kuffner et al. (2000) Pathway analysis in metabolic databases via differential metabolic display (DMD) Bioinformatics 16:825-836.

* cited by examiner

*Primary Examiner*—Mary K. Zeman
(74) *Attorney, Agent, or Firm*—Lynn E. Murphy; Lindera LLC

(57) ABSTRACT

The invention provides a computerized storage and retrieval system for storing biological information organized as a protein pathways database and methods for performing pathway searches on nodes (proteins or other molecules), modes (interactions), and nodes-and-modes. The protein pathways database is a relational database that integrates protein sequence, genomic sequence, gene-expression, protein interactions, protein-protein association and pathway data and can be searched using a query pathway to predict homologous or orthologous nodes, modes, and pathways.

13 Claims, 11 Drawing Sheets

METHODS FOR ESTABLISHING A PATHWAYS DATABASE AND PERFORMING PATHWAY SEARCHES

This patent application claims the benefit of provisional application 60/347,019 filed Jan. 7, 2002 and provisional application 60/269,711 filed Feb. 20, 2001.

TECHNICAL FIELD

This invention is in the fields of bioinformatics and molecular biology and relates to methods for establishing and using a pathways database to analyze data from biochemical pathways, sequence homology, protein interactions, and protein-protein associations.

BACKGROUND OF INVENTION

Proteins are primary components of the complex, interconnected pathways of cellular function. Proteomics, the study of protein location, interaction, structure and function, aims to identify and characterize the proteins differentially expressed in normal versus diseased biological samples. Abnormalities in protein production or function have been connected to many mammalian conditions, diseases and disorders. Therefore, the ability to identify proteins that cause or contribute to disease processes and to correctly supply or modulate these proteins represents an opportunity for therapeutic intervention. For example, oncoproteins can cause cancer by interacting with and activating proteins responsible for cell division in a manner that results in unregulated cellular growth. Protein interactions are also central to a virus recognizing its cell surface receptor prior to infection. Exact identification of such proteins and their interactions not only leads to a broader understanding of protein biology, but also provides the specific molecules that can be used to develop effective therapeutics.

Biochemical and genetic methods have been used to study protein interactions. The biochemical methods are laborious and slow involving numerous steps including isolation, purification, sequencing, and characterization of the proteins being tested for interaction. Small domains, regions within the proteins that fold independently, facilitate such interactions. Genetic approaches have gained in popularity in that they allow a more rapid detection of the domains involved in protein interactions.

The Human Genome Project (HGP) has produced vast amounts of sequence data for analysis. Numerous novel sequences, some of them conserved in diverse species, from *E. coli* to *Homo sapiens*, have been identified. The amount of data to be sorted, characterized and mapped has led to the development of numerous databases that contain genomic and protein sequence information. Parallel information explosions are resulting from biochemical studies of newly discovered proteins. Data on differential expression of these proteins has been widely collected for cells and tissues of many species under specific conditions. The mining of such data, mainly through homology searches, provides a broad view of how genes are expressed and in some cells and tissues, differential expression of mRNA is proportional to expression of the encoded proteins (Glavas et al. (2001) Proc Natl Acad Sci 98:6319–6324). Relating sequence data to protein pathways adds additional levels of complexity, but also identifies the best points for intervention in the disease process.

A pathway is a collection of at least two proteins or molecules connected by their interactions in a cell or tissue. Two pathways in the same species are called homologous if their proteins and/or interactions are similar; whereas the similar pathways are called orthologous if they occur in different species. Although the storage of information on protein interactions is at an early stage, additional tools for analysis of this information, methods for performing homologous and orthologous pathways searches and showing their relationships, are needed to handle the large amounts of information that will be stored in relational databases.

Bioinformatics capability and capacity will be needed to handle the sequence data produced from large sequencing efforts. For example, many large-scale sequence databases including NCBI GenBank (Bethesda, Md.) and SwissProt (Geneva, Switzerland) have been built to maintain current genomic and protein sequence information. Many sequence comparison packages such as LASERGENE software (DNASTAR, Madison Wis.) and specialized tools such as BLAST2 (Altschul et al. (1997) Nucleic Acids Res 25:3389–3402) and PHRAP (Phillip Green, University of Washington, Seattle Wash.) have been developed to study the sequences in these large databases. In addition, Hidden-Markov-Models (HMM, Pearson and Lipman (1988) Proc Natl Acad Sci 85:2444–2448) have been developed to work with proteins or with a protein families database such as the PFAM database (Washington University, St. Louis). For example, the SignalP program (Nielsen et al (1997) Protein Engineering 10:1–6) is an HMM that searches a given protein sequence for a signal peptide and its cleavage site. The pathways and bioinformatics above are discussed inter alia in Kanehisa and Goto (2000; Nucleic Acids Res 28:27–30); Nakao et al. (1999; Genome Inform Ser Workshop Genome Inform 10:94–103); and U.S. Pat. No. 6,057,101, which are incorporated by reference herein.

Although sequence homology has been the core of bioinformatic searches for many years, the more recent use of statistical clustering analysis has provided a major advance in the study of genes, proteins, and their function. The present invention satisfies a need in the art by providing methods for establishing a pathways database, that integrates data from biochemical or metabolic pathways, sequence homology, and expression data, and for using novel algorithms for optimization, dynamic programming, and constrained clustering with the pathways database to advance discovery of protein function and therapeutic intervention.

SUMMARY

The present invention provides a computerized storage and retrieval system of biological information comprising a means for data entry; a means for displaying the data; a programmable central processing unit for performing automated analysis; and a data storage means containing protein pathways and annotated information on the pathways and their proteins stored in a relational database, wherein the pathways are annotated and organized in a curated clustering arrangement and wherein the annotated information can be accessed through the relational database. The invention also provides for information pertaining to the pathways to be stored in a plurality of tables further comprising proteins, their sequences and attributes; protein interactions; protein-protein associations; protein pathways; mRNA, microarray, and protein expression data; genes, their sequences and attributes; and descriptions of cells, tissues, organs, pathology reports, patient histories, and treatments. In one embodiment, the central processing unit is programmed to retrieve, input, edit, annotate, search, calculate similarities, align, and predict homologous or orthologous protein pathways. In another embodiment, the central processing unit is programmed to perform protein sequence analysis, protein interactions analysis, protein-protein association analysis, protein pathway analysis, gene expression analysis, pathway annotation analysis, pathway edit analysis, pathway expression analysis, tissue expression analysis, subtractive hybridization analysis, electronic northern analysis, and commonality analysis. In one aspect, the data is entered into the computer system using a standard for pathway representation. In yet another embodiment, a means for displaying data is used to show two related pathways as a diagram containing nodes which represent proteins or non-protein molecules; modes which represent protein interactions or protein-protein associations; scores calculated from sequence, motif or structural homologies which interrelate nodes of the pathway; and coefficients of similarity which interrelate modes of the pathway.

The invention provides a method for performing pathway editing comprising programming the central processing unit of claim 1 to identify interactions among proteins; weigh the interactions; and calculate coefficients of similarity for the interactions, thereby producing an OS score for the protein pathway. The invention also provides a method of using genes which encode known proteins to annotate modes of a protein pathway comprising using standard algorithms and the data storage means to select genes which encode known proteins; employing the genes to produce a protein-protein association matrix containing coefficients of similarity; and annotating the modes of the pathway using the coefficients of similarity from the matrix. In one embodiment, annotations are inherited from a query pathway. The invention further provides for programming the central processing unit to compare two protein pathways by a node-only, a mode-only, or a node-and-mode comparison, wherein the node-only comparison is selected from protein only, non-protein only, and protein and non-protein nodes.

The invention also provides a method for protein pathways analysis using a node-and-mode comparison comprising submitting a query pathway and protein sequences; and allowing the computer system to compare nodes using the dynamic programming algorithm wherein a sequence identity score or p-value summarizes similarity and wherein a weighting factor between 0 and 1 is assigned to corresponding nodes; compare modes by generating a SCIM matrix, thereby assigning a coefficient of similarity to corresponding modes; align pathways globally or locally, wherein insertion or deletion of nodes or modes incurs a penalty; sum all similarity scores, and display at least one high-scoring segment of the aligned pathways. In one embodiment, the dynamic programming algorithm is supplemented by at least one standard method for protein and non-protein molecule comparison, wherein the methods are analysis of repetitious linear units, BLAST, BLOCKS, BLOSUM matrix, ClustalW, FASTA, HMM, INTERPRO, Needleman-Wunsch, PAM matrix, PRINTS, Prosite, RASMOL analysis, SCOP, and Smith-Waterman analysis.

The invention provides a method for performing protein pathways analysis comprising submitting a query pathway and protein sequences; and allowing the computer system to organize and analyze the query pathway and protein sequences, compare protein sequence identity of the query with all protein sequences in the protein pathways database using standard methods of protein comparison, use a SCIM matrix to derive and compare coefficients of similarity for each interaction of the query and all interactions for proteins in the protein pathways database, calculate an OS-score based on sequence identity and coefficients of similarity, remove all pathways not meeting user-specified threshold for OS-score, and retrieve all aligned pathways meeting the threshold. The invention also provides a method for searching a protein pathways database for a homologous protein comprising submitting a query pathway and at least one protein sequence; and allowing the central processing unit to perform protein sequence analysis between the submitted sequence and all protein sequences in the protein pathways database; and retrieving at least one homologous protein.

The invention provides a method for searching a protein pathways database for protein interactions comprising submitting a query pathway; allowing the central processing unit to perform protein interactions analysis between the query pathway and all protein pathways in the protein pathways database wherein coefficient of similarity is produced between each mode of the query pathway and a mode of the most closely related protein pathway; and retrieving at least one protein pathway alignment. The invention also provides a method of using a query pathway to search a protein pathways database to predict related pathways comprising submitting a query pathway and protein sequences; allowing the central processing unit to compare the query pathway and protein sequences with all protein pathways and proteins in the protein pathways database using standard methods of analysis, and retrieving a plurality of pathway alignments between the query pathway and protein pathways in the database wherein the alignments are arranged by OS-score, sequence similarity is shown between homologous nodes, and coefficients of similarity are shown between homologous modes. The invention further provides a method of using a known protein pathway and a protein database to predict orthologous pathways comprising submitting a query pathway and known protein sequences; allowing the central processing unit of claim 1 to compare known sequences to all protein sequences stored in the database, retrieving orthologous proteins with the highest identity to the known proteins, and aligning the query pathway and the orthologous proteins, thereby predicting an orthologous pathway.

The invention provides a method of using a known protein pathway to predict the nodes and modes of a novel pathway comprising submitting a query pathway and known protein sequences; applying standard methods of sequence comparison to determine similarity between the known protein sequences and protein sequences in the protein databases, thereby predicting nodes; utilizing protein interactions or a protein-protein association data to determine modes; and retrieving novel pathways with predicted nodes and modes based on OP-score. In one embodiment, the modes are determined using the methods of mRNA/cDNA counting, microarray expression, protein expression, known protein-protein associations, a promoter similarity matrix, or at least two of these methods. In a further embodiment, the method for predicting novel pathways uses a method for constrained clustering, wherein the clustering method is complete linkage, K-means, or self-organizing maps; the constraint is that no more than one protein in each cluster is derived from a single column of aligned proteins unless a very high penalty score is assigned during clustering; and the accuracy of the prediction is determined by an OP-score.

The invention provides a method for predicting novel pathways comprising generating candidate proteins from one species for each node based on a protein search; employing a means for optimization to find likely linear linkages between candidate proteins aligned to the query pathway with possible gaps in the alignment, and reporting all pathways with optimal and sub-optimal predictions that satisfy user-specified alignment and interaction parameters wherein the accuracy of the prediction is provided by OP-score. In one embodiment, the means for optimization is based on linear next-neighbor criteria, global minimization criteria, dynamic programming, or iterative searches using at least two of these means.

One implementation of the optimization algorithm using dynamic programming is depicted below. It comprise initializing an array, in which a two dimensional array $M=M_{ij}$ with J rows and variant length for each row, the length for i-th row is $n_i$ is set up and $M_{ji}=0$, where $1<=i<=n_j$, backfilling the array via backward recursion with the formula $$M_{ik} = \max_{\substack{j>i \\ 1 \leq l \leq n_j}} \{w(a_{ik}, a_{jl}) + M_{jl}\theta(w(a_{ik}, a_{jl}))\}$$

$$\text{for } 1 \leq k \leq n_i, 1 \leq i \leq J$$

where $\theta(.)$ is the step function defined as $\theta(v)=\{0, \text{ if } v<=0; 1, \text{ if } v>0\}$ and $w(.,.)$ is the scoring function between the two nodes, defined as $$w(a_{ik}, a_{jl}) = \begin{cases} 0, \text{ if } i = j, a_{ik} = a_{jl}, a_{ik} = -D, \text{ or } a_{jl} = -D \\ \theta(c_{ik,jl} - t_c) \cdot \{\alpha(1 - |s_{ik} - s_{jl}|) + (1-\alpha)c_{ik,jl}\} \text{otherwise,} \end{cases}$$

$$\text{and } D > 0$$

using traceback to identify putative pathways $PPW_j$, $1<=j<=\max n_i$ with the top n best scores. One can also report sub-optimal hits that deviate slightly from the optimal hits.

The invention also provides a method for determining the function of a protein or a gene that encodes the protein comprising placing the protein encoded by the gene in a candidate pathway involving at least two proteins, and using dynamic programming and the data storage means wherein the interactions with proteins and non-protein molecules, cellular location, and expression are used to determine the function of the protein or gene.

The invention provides a method for using a computerized storage and retrieval system of biological information to predict novel pathways comprising submitting a query pathway and protein sequences; and processing the query pathway and protein sequences using orthologous pathway prediction wherein the data is derived from protein interactions, or homologous pathway prediction wherein the data is derived from protein interactions and protein-protein associations obtained from a dynamic programming algorithm or a constrained clustering algorithm.

One implementation of constrained clustering algorithm is depicted below. It is a modified form of traditional distance-based clustering methods. Constrained here means that: 1) the predicted pathway will have at most one member from each column; 2) known interactions between proteins can be incorporated into predicted pathways, over-writing the expression-correlation data. Every pair of proteins in the database is assigned a distance that satisfies the constraints, and suggests the likelihood of being in the same pathway. Initially, every $$d(c_1, c_2) = \left\{ \frac{1}{n_1 + n_2} \sum_{i \in c_1} \sum_{j \in c_2} d_{ij}^p \right\}^{1/p}$$

point is its own cluster. At each round, we merge the two closest clusters. Clusters are merged until the final clusters are too far apart to merge (threshold set by the user). The distance between two clusters is computed by various formulae. For example, in mean linkage, the distance is a weighted average of the old distances. ($n_1$ is the size of $c_1$; $n_2$ is the size of $c_2$)

Mean linkage is a special case of $l_p$-linkage, in which distances are combined by a weighted average of powers. $l_p$-linkage is mean linkage when p=1, and approaches complete linkage in the limit as p->infinity. In practical terms, the constraints are satisfied by manipulating the distances involved: 1) proteins that are in the same column get a high distance; 2) proteins known to be in a common pathway get zero distance; 3) otherwise, the distance between database proteins i and j is a function of: 1) similarity to query protein ($s_i=S_{iq(i)}, s_j=S_{jq(j)}$), where q(i) is the query protein homologous to database protein i, 2) protein-protein association ($a_{ij}$).

$$d_{ij}=\alpha(1-\alpha_{ij})+(1-\alpha)|s_i-s_j|$$

The invention also provides a method for using a gene that encodes a protein of a predicted pathway to confirm expression of the protein in a biological sample comprising using standard methods and the data storage means to select the gene which encodes the predicted protein, designing oligomers to the gene, employing the oligomers in QPCR to measure mRNA expression in the sample, and comparing expression to positive and negative controls, wherein expression indicates the presence of the protein in the predicted pathway.

DESCRIPTION OF THE INVENTION

Definitions

Figure 1:
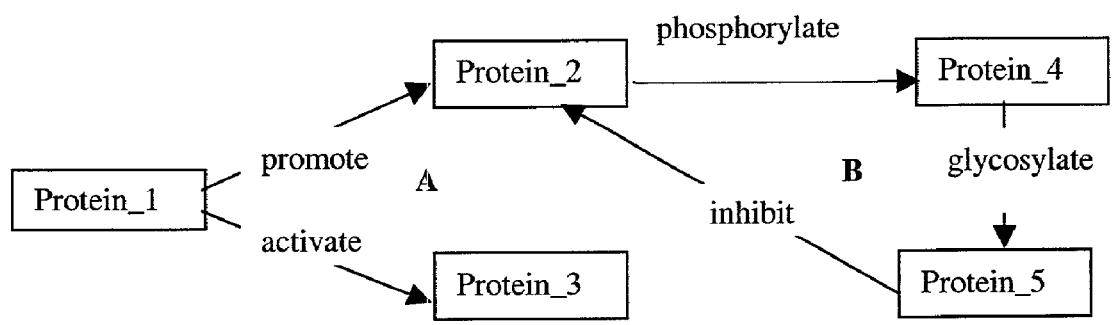
FIG. 1. A pathway diagram showing a pathway of nodes and modes, bifurcations, and feedback loops.

"Alignment" refers to global or local alignment of molecules or pathways.

An "attribute" when used with proteins refers to protein motifs, domains, and structural features such as three-dimensional folding that are of significance in naming, categorizing and determining the function of the protein; and when used with polynucleotides refers to binding sites, introns, untranslated terminal regions, methylation, and structural features that regulate activities such as transcription, translation, and replication.

The "direction of interaction" schematically indicated by an arrow and a word describing some biological or enzymatic activity refers to the interaction that occurs between any two nodes, proteins, or molecules.

A "gene" is a segment of a genome that has a physical location in the genome, is composed of exons, introns, a promoter, and untranslated regulatory regions and expresses at least one functional protein.

A "hit" refers to a result—a protein, an interaction, or a pathway—that matches a user query and that satisfies a user-specified threshold based on identity, similarity or species-of-interest.

"Identity mapping" refers to a process for assigning a score to the comparison of two nodes; when the molecules are identical, the score is 1, and when the molecules differ, the score is 0.

A "mode" is any interaction that connects two nodes. It indicates uni- or bi-directional interactions and is described using words such as activate, associate, carboxylate, coactivate, deactivate, decarboxylate, deglycosylate, dehydroxylate, dephosphorylate, downregulate, generate, glycosylate, hydroxylate, inhibit, phosphorylate, promote, stimulate, upregulate, and the like.

A "node" is a component of a pathway, a protein or non-protein molecule including, but not limited to, inorganics such as atoms, ions, cofactors, prosthetic groups and side chains; organic molecules such as carbohydrates, lipids, fats, steroids, cyclic nucleotides, and compounds such as glycoproteins, glycolipids, NADH; and small drug molecules and the like that may have repetitious linear units and carry out a particular function in particular cellular location.

"Orthologous" refer to two or more proteins or pathways from different species that have the most similar function.

"OS-score" refers to overall-similarity score that is calculated and normalized using node and mode similarity scores and that serves to index the similarity between two pathways.

"OP-score" refers to overall-predicted score that is calculated during the prediction of novel pathways using PMpredict and that serves to index the similarity between two pathways.

A "pathway" refers to a plurality of nodes connected by modes, and each pathway must contain at least two nodes and at least one mode.

"Patient history" refers to those data in a patient's medical record which include age; sex; conditions, diseases, disorders, or syndromes of the patient or relatives of the patient, particularly grandparents, parents, or siblings; and past or current treatments of the patient for any of the conditions, diseases, disorders or syndromes.

A "protein" is a structural or enzymatic molecule composed of amino acids that is transcribed and translated from a gene. A protein may have variants resulting from expression of mutational changes such as deletions, additions, and substitutions of one or more nucleotides in the gene or from alternative mRNA splicing.

A "query" refers to a search that can be performed at the protein level (node-only where the OS-score is calculated by node similarity only), at the interaction level (mode-only where OS-score is calculated by mode similarity only) or at the pathway level (pathway where OS score is calculated using both node and mode similarities).

A "sample" refers to a bodily fluid; the soluble fraction of a cell preparation; an aliquot of media in which cells were grown; a chromosome, an organelle, or membrane isolated or extracted from a cell; genomic DNA, RNA, or cDNA in solution or bound to a substrate; a cell; a tissue or tissue biopsy; a tissue print; buccal cells, skin, or hair which contains nucleic acids or proteins.

"SCIM" matrix refers to a matrix that represents similarities among protein interactions. Two distinct modes, or interactions, are identical where the coefficient is 1, associated positively when the coefficient is >0, and associated negatively when the coefficient is <0.

"Standard methods" for comparison include, but are not limited to, analysis of repetitious linear units, BLAST, BLOCKS, BLOSUM matrix, ClustalW, FASTA, HMM, INTERPRO, Needleman-Wunsch, PAM matrix, PRINTS, Prosite, RASMOL analysis, SCOP, and Smith-Waterman analysis.

A "uni-protein database" refers to a collection of proteins from at least one species, but preferably from several species, where redundancy is minimized by categorizing splice variants as separate, dependent entries.

THE INVENTION

The invention provides methods for establishing a protein pathways database and methods for querying the components of that database, primarily the nodes (proteins or non-protein molecules), the modes (interactions between nodes), and the biochemical or metabolic pathways in which the nodes and modes occur. The database encompasses protein sequences and their variants, nucleotide sequences (genomic, cDNA, and EST) and their variants, data from gene expression studies, data from the scientific literature and public databases, and biochemical and metabolic pathways. Pathways are viewed as collections of interacting proteins or other molecules, and a pathway is shown as a diagram where the nodes are linked via directional lines that represent the modes. Even though any particular diagram can only be shown in one dimension, the nodes and modes can show bifurcations and feedback loops. Since every protein can have numerous interactions with other proteins, a pathway need not have an endpoint. However, for clarity, a particular pathway is shown as having boundaries that define either the extent of scientific knowledge, interest, or focus.

A typical example of a pathway is shown in FIG. 1. Each of the boxes represents a node, and the nodes, in this case, are proteins 1 through 5. The arrows between nodes represent modes that are the specific interactions between any two proteins or molecules. Note that the pathway includes both a bifurcation, between node 1 and nodes 2 and 3 and a feedback loop which begins and ends with node 2. As shown in the diagram, node 1 has 2 modes, and node 2 has three modes. The arrow and a word describing some biological or enzymatic activity are found between any two nodes and indicate the nature and direction(s) of the known interactions. As used herein, the word describing the biological or enzymatic activity is qualitative rather than quantitative. Although not shown here, cellular location can be indicated at a node in a pathway diagram.

Figure 2:
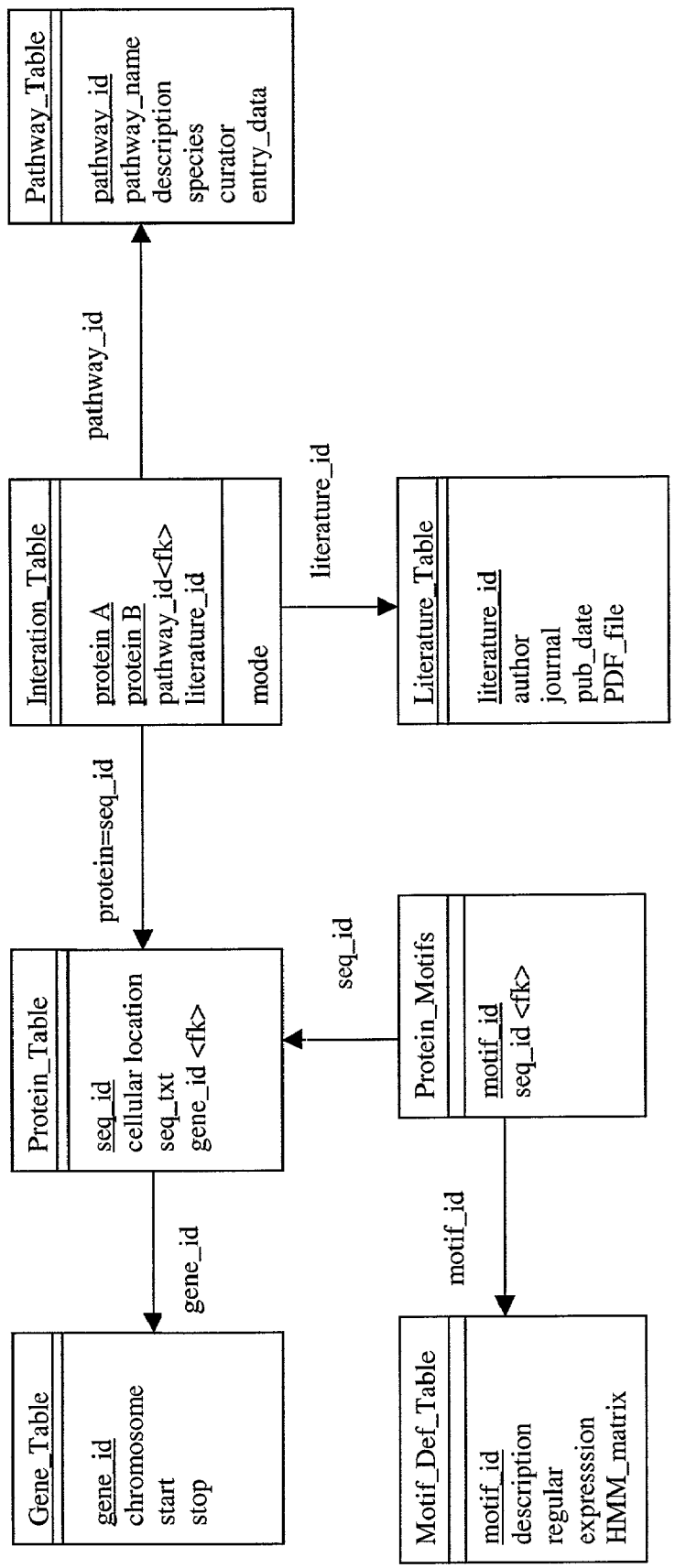
FIG. 2. An example of the types of tables stored in a relational protein pathways database.

The protein pathways database is organized as a relational database; it contains distinct tables for the pathways, nodes, modes, sequences, variants, expression data, literature, motifs, and other types of information about the proteins and their interactions. FIG. 2 shows an example of some of the kinds of tables in the relational database; attributes are shown under the name of each table. Abbreviations used in the tables include seq (sequence), $_{13}$ id (ID or identification), $_{13}$ txt (text), $_{13}$ def (definition), and <fk> (foreign key).

The Pathway$_{13}$ Table contains the attributes: pathway$_{13}$ id, pathway name, description of the pathway, species, curator, and the like. The nodes are recorded in the Protein$_{13}$ Table that contains the attributes: seq$_{13}$ id, cellular location, seq$_{13}$ txt, and gene$_{13}$ id<fk>. The Interaction$_{13}$ Table which links the protein and pathway tables must contain at least two proteins and one mode. Surrounding the protein, interactions, and pathway tables are tables containing supporting data such as the Literature$_{13}$ Table, the Protein$_{13}$ Motifs, and Gene$_{13}$ Table.

Figure 3:
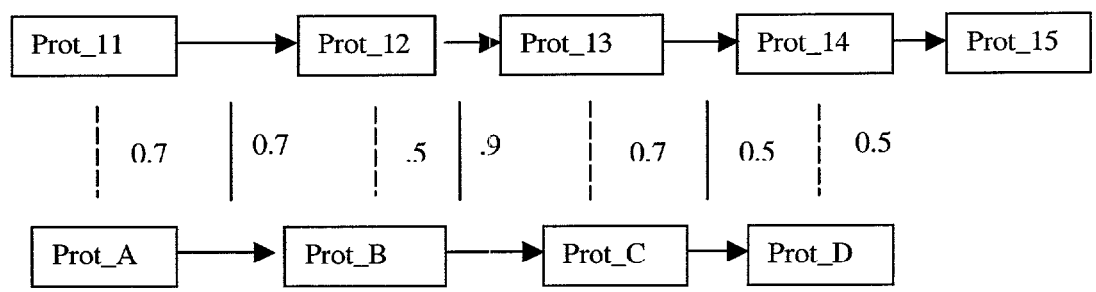
FIG. 3. An example of node and mode pathways alignments.

Pathways in the database can be aligned at three different levels, node-only alignment, mode-only alignment, and node-and-mode alignment. These alignments are shown in FIG. 3. In a node-only alignment, the similarities among the nodes, a calculation made using standard methods of sequence comparison, are shown as dotted vertical lines and associated values between two aligned nodes. The most common comparison is the comparison between two protein sequences. For example, a Smith-Waterman sequence comparison (Smith and Waterman (1981) J Mol Biol 147: 195–197) can be performed to assign a score for sequence identity or similarity between any two proteins. Other means for sequence comparison that are well known in the art include BLAST, BLOSUM matrix, FASTA, BLAST, ClustalW, Needleman-Wunsch global alignment, PAM matrix, SCOP, and Smith-Waterman analysis. Alternative methods for comparing or characterizing proteins include HMMs, Pfam models, motif searches and alignments using BLOCKS (Henikoff and Henikoff (1991) Nucleic Acids Res 19:6565–6572), PRINTS (Attwood et al. (2002) Nucleic Acids Res 30:239–241), PROSITE (Hofmann et al. (1999) Nucleic Acids Res 27:215–219), and INTERPRO (Apweiler et al. (2001) Nucleic Acids Res 29:37–40), and three dimensional structural comparisons such as structural classification of proteins (SCOP) or RASMOL analysis (University of Massachusetts, Amherst Mass.).

If the node is not a protein, but another molecule, the comparison can be based on identity mapping. For example, the identity assigned between a lipopolysaccharide (LPS) molecule in one species and an identical LPS molecule in a second species is 1 and between a LPS molecule from one species that is homologous to a LPS from another species is 0. Such comparisons are chemically and/or structurally based and can be used with proteins that have undergone post-translational modification or with molecules such as carbohydrates, lipids, fats and the like.

The mode-only alignment is calculated using the SCIM matrix and is shown as a vertical solid line and associated score between two aligned modes. A SCIM matrix presents the coefficient of similarities among the interactions. Two distinct modes can be associated positively (where the coefficient is >0) or negatively (where the coefficient is <0), or they can be identical; in which case, each coefficient seen on the diagonal is 1. In most cases the number is between −1 and 1 indicating that the two modes are either positively or negatively associated. The simple table below shows a SCIM matrix.

| Modes | activate | downregulate | phosphorylate |
|---|---|---|---|
| activate | 1 | 0.75 | 0.5 |
| downregulate | 0.75 | 1 | 0.67 |
| phosphorylate | 0.5 | 0.67 | 1 |

The SCIM matrix is comparable to PAM and BLOSUM matrices for protein comparisons, but it is used to calculate similarities between interactions in different pathways. The coefficients necessary to produce a useful SCIM matrix are derived statistically from known pathways. Both node and mode alignment scores are tallied to produce the OS-score that accounts for similarity at both the protein and interaction levels and is used to quantify the similarities between pathways. One aspect of the invention is that each pathway has a unique ID and is treated as a unit, not just a relationship among protein interactions. In this way, two pathways can involve the same proteins, but can be queried for different interactions or associations between any two proteins. The OP-score tallies similarities between pathways using interactions and/or protein-protein associations.

Establishing a Pathways Database

The protein pathways database of the invention is a relational database. The pathways database is constructed by collecting and storing charts of known biochemical and metabolic pathways, and tables of proteins and their attributes, genes and their attributes, expression data, and the like for each species and protein of interest. The species may include, but are not limited to, human, dog, rat, mouse, zebrafish, *Drosophila, Caenorhabditis elegans, Arabidopsis thaliana, Saccharomyces cerevisiae, Escherichia coli* and the like. As shown in FIG. 2, both the pathway and sequence tables are labeled according to species, and the tables are linked through unique sequence and pathway IDs. The pathways for a particular species can reside in a species-specific database or be combined into the pathways database.

Building and Curating a Uni-Protein Sequence Database for Each Species

To facilitate pathway search algorithms, a "uni-protein sequence database" is needed for each species. A uni-protein sequence database contains minimal redundancy for each protein in the database. For example, for a typical protein with 10 entries in a database, two are identical full-length proteins, five are partial sequences, and three are splice variants. In the set of "uni-protein sequences", only one full-length protein and the three splice variants are retained; all other sequences are deleted.

Hand-curated databases, such as SwissProt, are "uni-protein" databases. In SwissProt, the database provider removes any redundancy by checking each individual entry. Similarly, NCBI has used automation to remove redundancy from the UniGene database (Shuler (1997) J Mol Med 75:694–698); however, they have not associated the corresponding protein sequences with each cluster of nucleotide sequences. This process can be carried out in an automated fashion using selected criteria for "uniqueness" and some level of human intervention for extremely complex cases. This invention uses an automated process to provide a uni-protein sequence database for each species of interest.

Queries Using the Protein Pathways Database

The queries that can be made using the database and/or its components are summarized below.

| Database | Queries |
| --- | --- |
| Pathway_db | Node-only, mode-only, and node-and-mode |
| Uni-protein_db | Node-only |
| Uni-protein_db and protein-protein association matrix | Node-only, Node-and-mode |

The simplest query is a search using a query pathway and protein sequences against the pathways database. The search engine can be used at mode-only level, node-only level, or mode-and-node levels. The queried database can be a pathways, protein, interactions or protein-protein association database. Node-level queries are based on sequence homology, and mode-level queries are based on similarities for the various documented interactions. The protein-protein association matrix is based on gene expression studies including transcript images, clone counting of cDNAs, ESTs, promoter regions, or regulatory sequences expressed in or associated with a particular tissue or from microarray data, immunoprecipitation, from yeast two hybrid data, from quantitative real-time PCR (QPCR), and the like. Periodically, information from a protein-protein association matrix is curated and entered into the protein-protein association database.

Node-only comparisons: When the database to be searched is a protein sequence database, then a node-level search is performed. The query pathway is used to find homologous or orthologous pathways. The best search results will come from the most complete uni-protein databases. Since sequence similarity is the only criteria for the node-only search, the modes of the aligned, or hit, pathway are inherited from the query pathway, and only one pathway is expected per species. The final output is a pathway diagram for each species with scores above the specified threshold.

Node-and-mode comparisons: A more powerful query is a pathway query using both nodes and modes. This search uses sequence information to find candidate nodes and protein interaction or protein-protein association matrix information to find candidate modes. The resulting report will present all homologous and orthologous pathways based on OS-score.

In a typical "pathway search", a query pathway is selected or submitted by a user. The query pathway can be a pathway from a pathways database, a metabolic or biochemical chart, the literature, or the user's research. The query pathway must specify the species, the proteins, and some interactions among those proteins. The components need to be linked together to form a "pathway diagram" following the format shown in FIG. 1.

If a query pathway is imported from a pathways database, the user can use the pathway$_{13}$ id, and the computer will retrieve the pathway and protein sequences automatically. If the user wants to query a unique or hypothetical pathway, the computer software can be used to specify one component at a time. The computer is programmed to display the query pathway in a format understood by one of skill in the art.

FIG. 3 is a diagram showing two aligned pathways. The five nodes of the query pathway are numbered proteins 11→15, and the aligned orthologous pathway has four nodes with proteins A→D. Percent identity between nodes is shown beside the dashed line that interconnects any two nodes, and calculated similarity between modes is shown beside the solid lines that interconnect any two modes. Although not shown here, the OS-score for the pathway is calculated from node and mode similarity scores.

Figure 4:
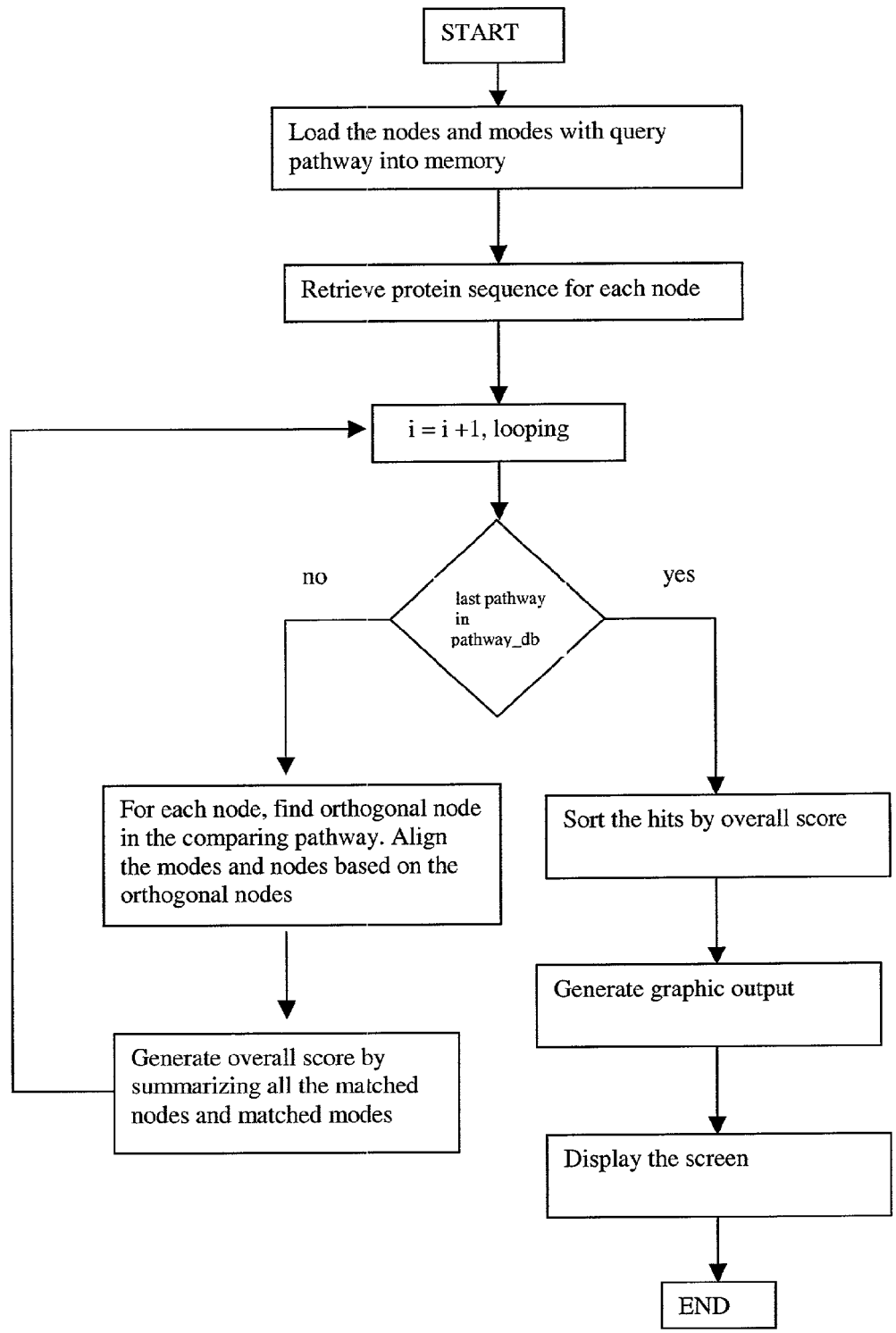
FIG. 4. A block diagram showing a pathway query of a pathways database.

FIG. 4 is a block diagram demonstrating the logical steps for a pathway search. First, the query pathway and all nodes and modes are retrieved, or if submitted by the user, standardized, and stored in memory. Second, the nodes are compared to all other nodes in the pathways database by calculating percent identity between a protein or molecule of the query and each of the proteins or molecules stored in the database. Percent identity is used to match orthogonal nodes between pathways and to calculate the OS-score. This process is reiterated until all pathways in the database have been compared with query pathway, and computer default or user-specificied thresholds are met. All statistically significant matches are sorted by OS-score and displayed one after another on the computer screen in the format previously presented in FIG. 3.

Figure 5:
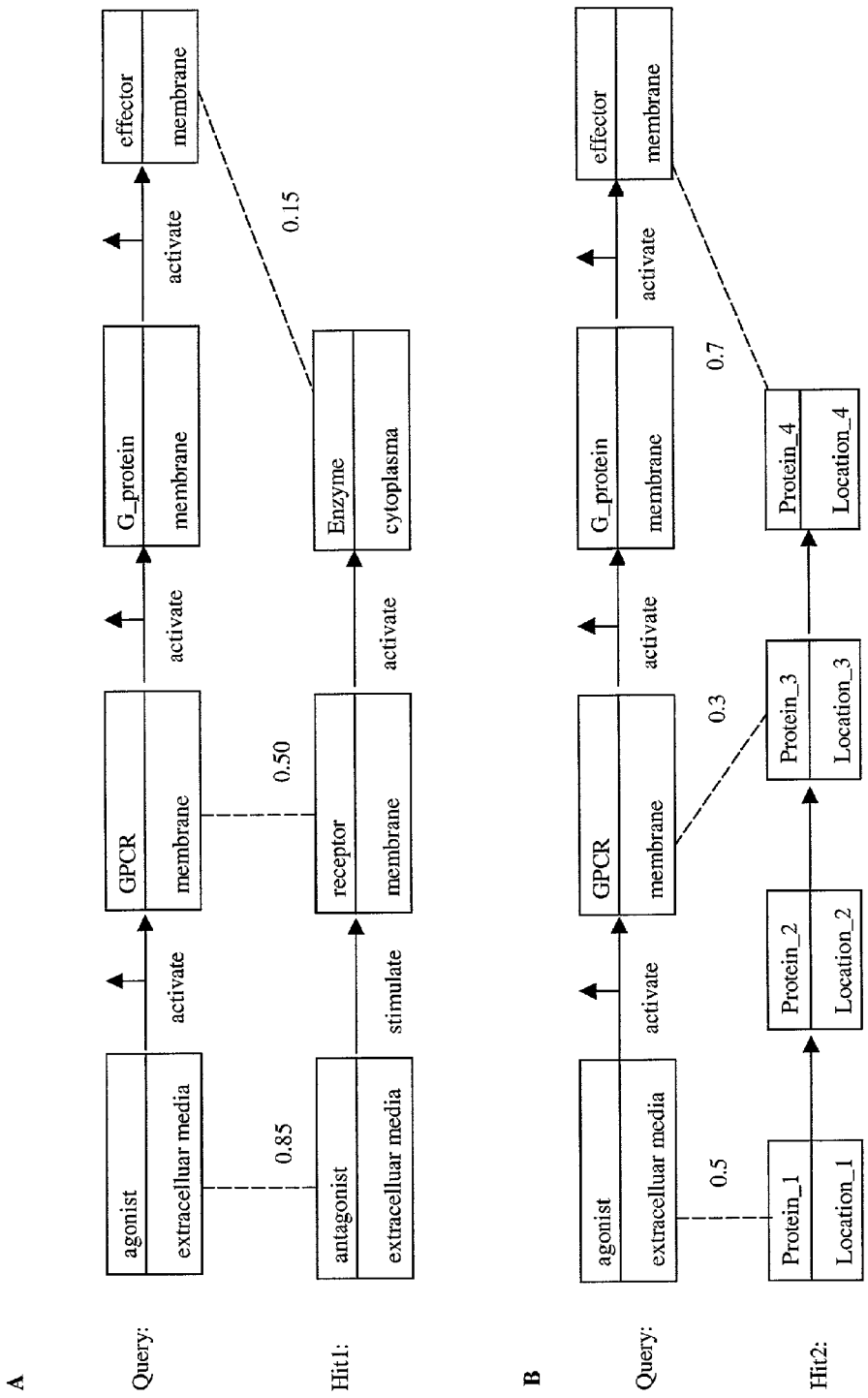
FIG. 5. Sample output of a node-only query of a pathways database.

FIG. 5 shows the results and alignments of two high-scoring pathways for a pathway query against a pathways database, with a node-only search. The results compare two pathways at the node-only level by mapping the orthologous nodes and modes between the two pathways. FIGS. 5A and 5B show two high-scoring alignments, hit1 and hit2, respectively, with the query pathway using a node-only search. When the sequence similarity score (percent-identity) is above threshold, it is recorded beside the dashed line which links corresponding nodes. Note that cellular locations are given for each of the nodes in FIG. 5A, but are not available for the second best alignment shown as FIG. 5B. When multiple pathways meet threshold, the alignments are sorted by OS-score and displayed one after another on the computer screen.

The on-screen alignments for the mode-only search is very similar to the above description. For a mode-only search, a dashed line and similarity score is shown for each of the corresponding orthogonal modes, but no alignment is shown for the nodes. Similarly, the on-screen alignments of a mode-and-node queries of the pathways database, dashed lines and their respective similarity scores link corresponding orthogonal nodes or modes. OS-score is used to rank the pathway alignments which meet threshold and are reported on-screen.

Figure 6:
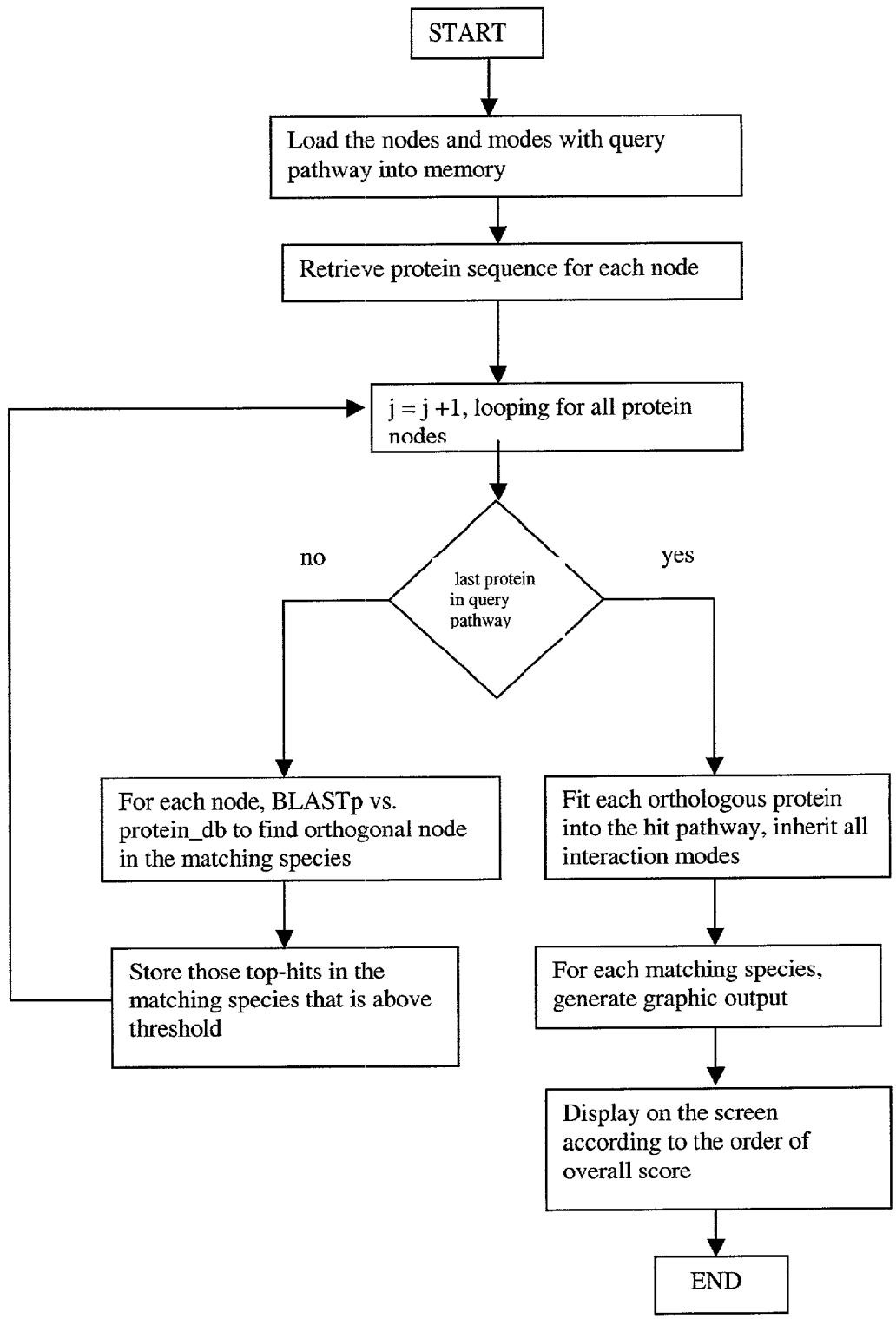
FIG. 6. A process diagram of a node-only orthologous pathway search.

Orthologous queries: FIG. 6 is a block diagram of the logical steps for an orthologous pathway search. In the simplest "orthologous pathway search", the user specifies a query pathway from one species and searches the pathways database against at least one other "target" species. Although the aligned pathways will show the exact same modes for both species because the interactions are inherited, the identity of each protein in the target species is determined by a sequence search against all protein sequences in the database. At least one standard method for sequence comparison is used to provide the best alignment for each query sequence. Once all sequence queries are completed, candidate proteins from the target species are lined up and shown in the same formal as the query pathway. Additional sequence statistics such as p-value or percent identity can be shown next to the sequence_id. Exact sequence alignment is accessed by clicking the computer mouse pointer on any of the statistical data.

Figure 7:
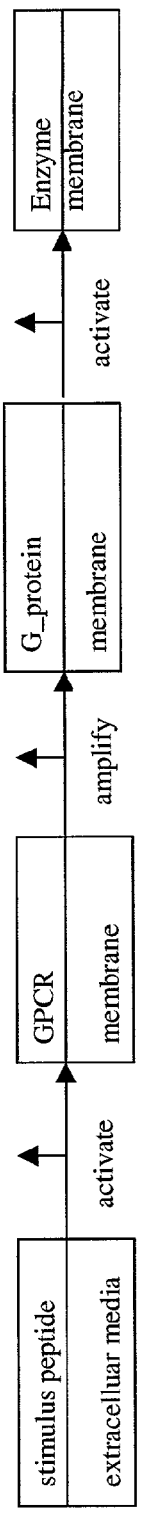
FIG. 7. A sample output from a node-only orthologous pathway search.
Figure 7:
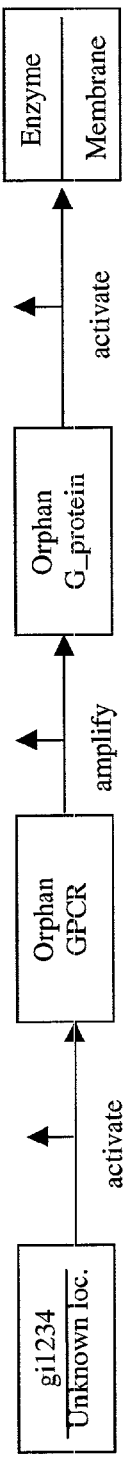
Figure 7:
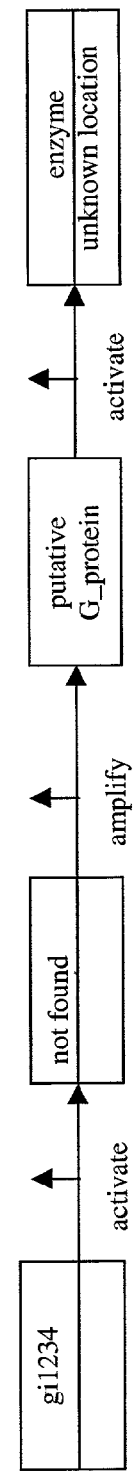

If two or more proteins in the target species protein database meet threshold, then, the pathway diagram has to be modified. Although each species is presented in its own alignment, all candidates for the orthologous pathway are presented sequentially so that the user can evaluate and select the alignments of greatest interest. FIG. 7 shows a sample output from a node-only, orthologous pathway search. The query pathway is from one species and is searched against uni-protein sequence databases for all other species. Orthologous nodes are selected from best BLASTp alignments, and all modes are inherited from the query pathway on the assumption that in closely related species or in evolutionarily conserved pathways, they are likely to be the same.

In FIG. 7, the query pathway is from *Homo sapiens*, and the orthologous alignments are from *Mus musculus*, and *Saccharomyces cerevisiae*. Not all nodes are matched with nodes in another species, especially where two species are more evolutionarily distant. Nodes without an ortholog are represented by empty rectangles and serve as a reminder that inherited interactions are more tentative than known interactions.

Searching Against a Species Using a Uni-protein Database and a Protein-protein Association Matrix In this approach, expression data from electronic northern analysis of sequences in the public databases or microarray data are used to analyze protein-protein association and produce a protein-protein association matrix. The matrices are periodically curated and stored linked to the protein in the uni-protein database for the species. An expression database is a collection of data, where for each specific tissue, there is a relative expression level for each gene. Only about 10% of all genes in a species are expressed in any specific tissue at any point in time, thus for the other 90% of the genes, tissue expression is zero. If the user does not limit the query to a specific tissue, all expression data from all tissues are used.

To produce the protein-protein association matrix, a correlation coefficient is calculated using the dynamic programming algorithm for two proteins in the query pathway, then additional correlation coefficients are calculated for each of the other proteins in the pathway, two at a time. Beginning with the first protein in the pathway, the most likely candidate for the second protein is chosen using the highest correlation coefficient with a value closest to one. This process is repeated, one protein at a time, until all proteins have been analyzed, and the correlation coefficient no longer meet the user-specified threshold. The process is reiterated beginning with the second protein, and then the third, until all protein associations have been examined. The result or output from this process is a collection of pathway diagrams; and some output pathways are shorter than the query pathway, because no proteins pass the specified threshold.

In one embodiment, the user may want to use the invention to find all homologous pathways for a given query pathway within a species. In another embodiment, the user may want to find out all the orthologous pathways in a collection of species. This search is more complex than earlier searches because heterogeneous information must be integrated; however, information from sequence identity or from protein-protein association alone is insufficient to find homologous and orthologous pathways. Only when information from both sources is combined is it possible to find the best pathways.

As in the previous example, a node-only search is performed for each of the proteins in the query pathway. After the sequence comparisons are completed, all significant candidate proteins are presented for each node. The node-only diagram is processed into a collection of smaller diagrams using additional information from protein interactions and/or from the protein-protein association matrix for each species.

Figure 8:
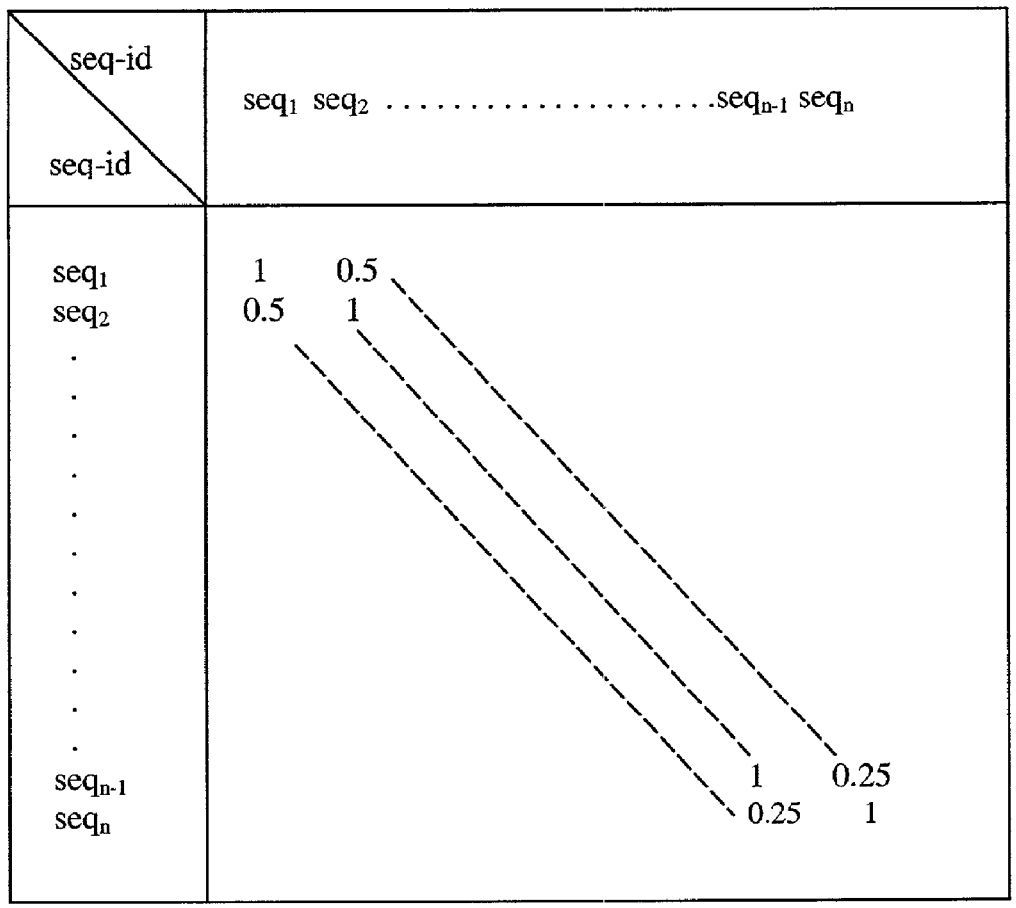
FIG. 8. A protein-protein association matrix obtained from expression data.

FIG. 8 shows an example of a protein-protein association matrix obtained through analysis of protein associations derived from expression information. With this matrix, the exact nature and direction of interaction may be unknown, but any two proteins with a significant correlation coefficient are in the same pathway even if they have no direct interaction. The matrix shows the relationship among the proteins within a tissue produced using expression data available from public dbEST databases or from microarray data. The more specific the tissue, experimental conditions, and time points, the more accurate the association matrix. Although information from genes or mRNAs (or their cDNAs) are preferred, information from promoter-region sequences and other regulatory regions in a genome can be used in an association matrix. If a gene is always strongly associated with another gene, the likelihood that those two genes are involved in the same pathway is greatly increased. As shown in FIG. 8, the coefficient is always 1 on the diagonal line because a protein is always 100% correlated with itself, and the matrix is symmetrical.

Figure 9:
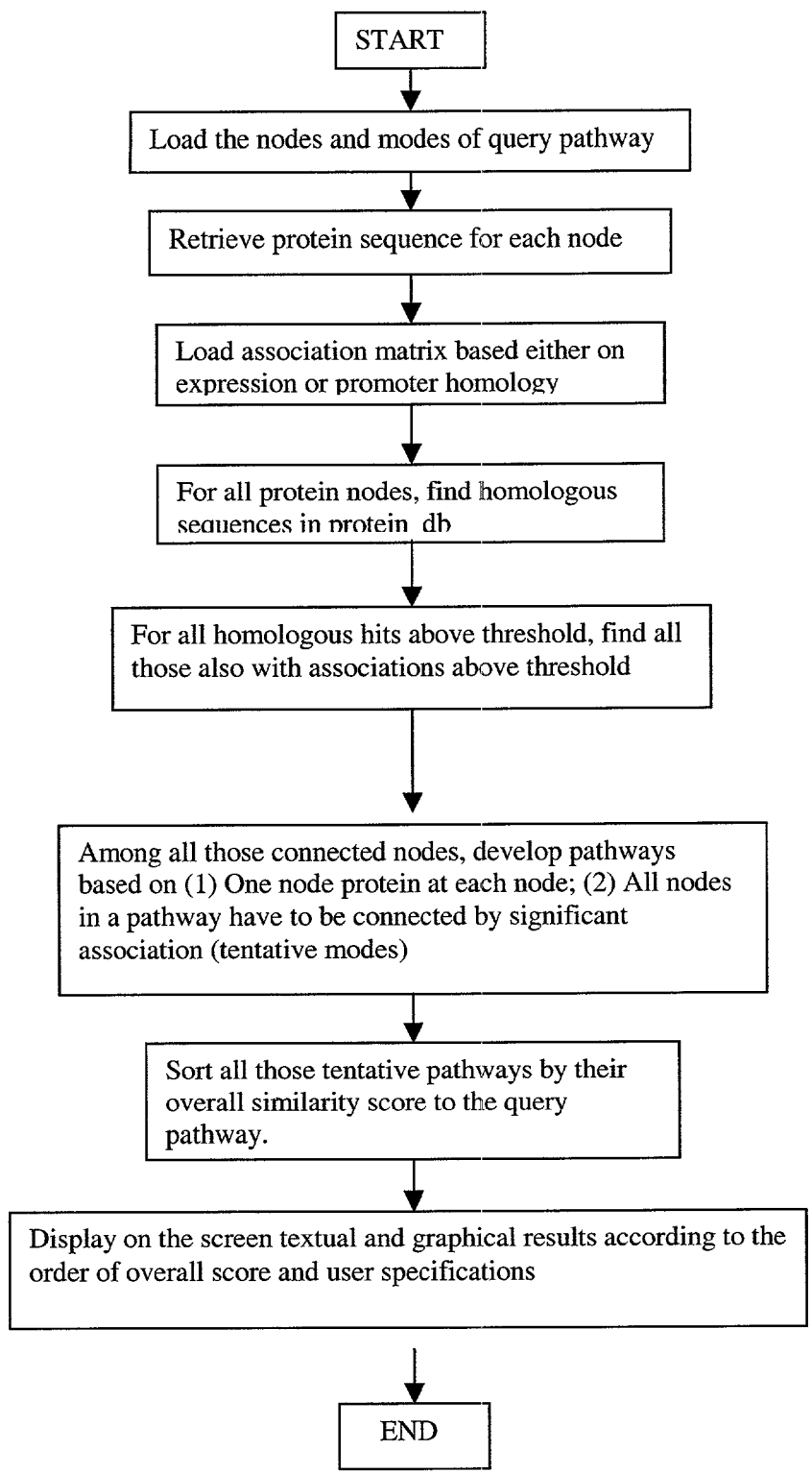
FIG. 9. A block diagram of node-and-mode pathway search.

FIG. 9 shows the block diagram of node-and-mode pathway search using a uni-protein database and a protein-protein association matrix. For a given query pathway, the uni-protein database and matrix are for a single, user-selected, species-of-interest. For a given query pathway, the nodes and modes and their association matrices are loaded into memory. Homologous proteins, selected for each node using standard methods of comparison, become candidate nodes for constructing the pathways. The candidate modes are those coefficients of similarity from the protein-protein association matrix or SCIM matrix that satisfy mode-similarity threshold. For each candidate node, a direction of interaction is assigned when the number of candidate modes linking the node to a neighboring node(s) is a small number, preferably one. Homologous or orthologous pathways are reported on screen as diagrams when the node and mode scores are sufficient to calculate an OS-score or an OP-score that exceeds the user-specified threshold.

Figure 10A:
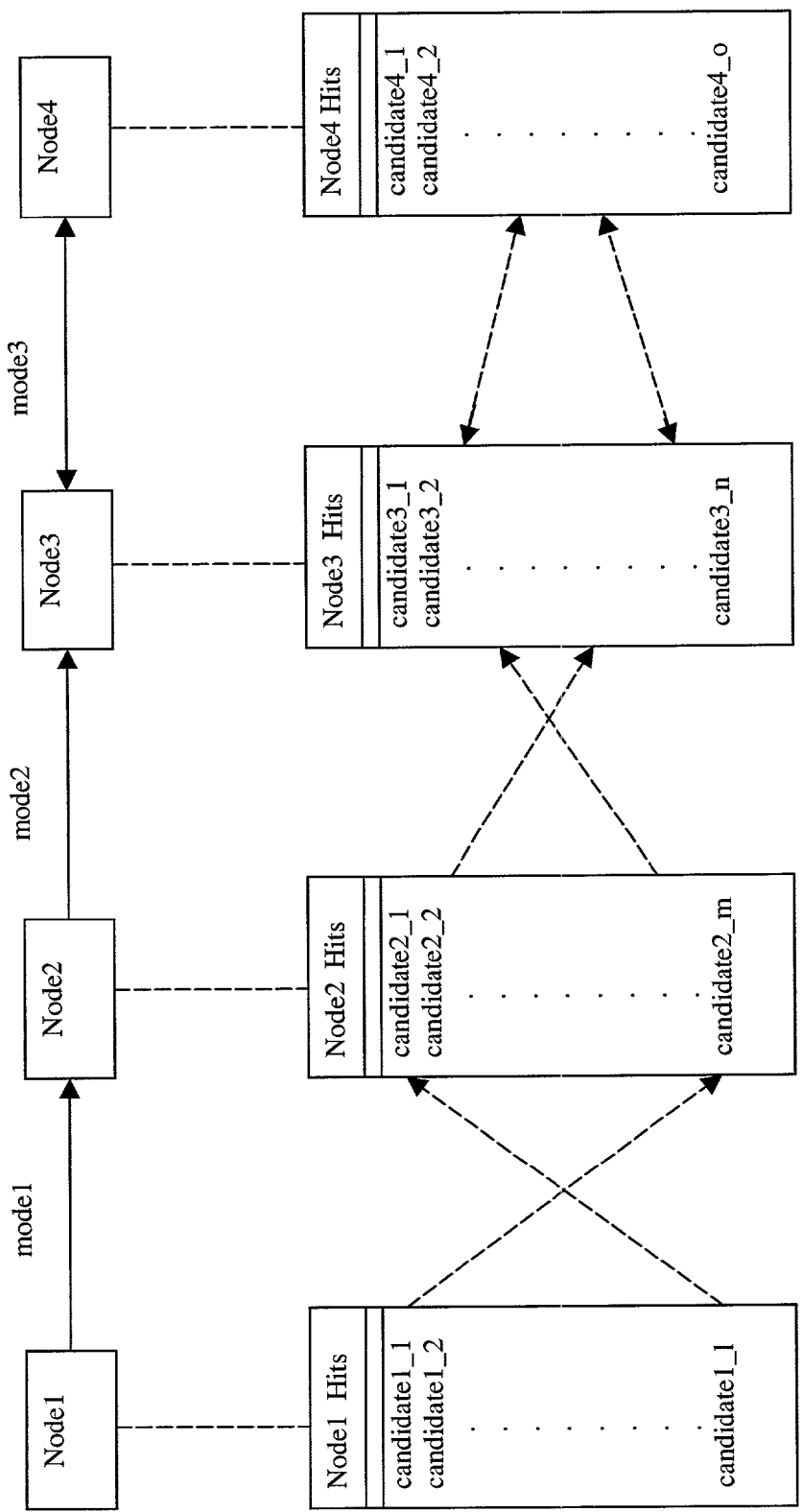
FIGS. 10A and 10B. Results of a node-and-mode pathway search employing a uni-protein database and protein-protein association matrix.
Figure 10B:
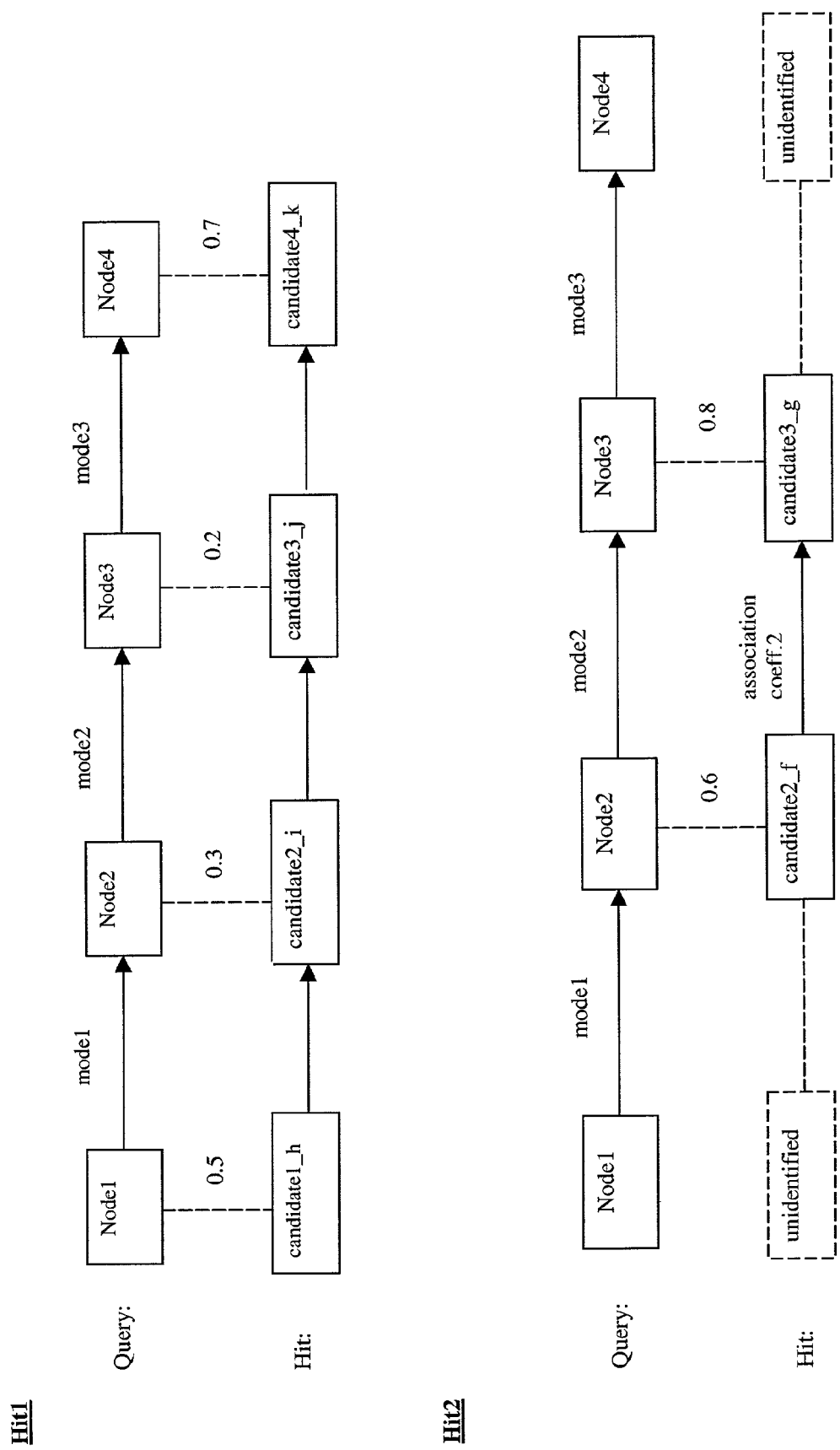

FIG. 10 shows the output from a pathway search at node-only level employing uni-protein database and protein-protein association matrix. FIG. 10A shows an intermediate step in such a search in that each node has multiple candidate proteins with unknown interactions. After the information from the protein-protein association matrix is taken into account, proteins with correlation coefficients above threshold (positive or negative) are indicated by dashed arrows. FIG. 10B shows two aligned pathways that satisfy user-specified thresholds. Output pathways are reported on-screen in the order of OS-scores.

The protein-protein association matrix based on expression data can be replaced with a promoter-region or regulatory region similarity matrix. For example, one can construct a promoter-region similarity matrix for a collection of genes from a species. There are patterns or similarities within the promoter region, and one promoter can actually regulate many genes within the same pathway. A promoter-region or regulatory region similarity matrix can only be used to detect positive associations that are very strongly correlated, i.e., the genes being transcribed are co-expressed at the same time. Weak or negative associations are unlikely to be detected.

If protein interaction data for a species is well known, then a SCIM-matrix is constructed and used to perform the "node-and-mode" search. Protein interaction is much more reliable than protein-protein association although the latter can be used to perform node-only searches and to supplement node-and-mode comparisons. Protein interactions are derived from biological research, such as immunoprecipitation, yeast-two-hybrid, or QPCR investigations, where protein interactions are systematically tested. When both protein interactions and protein-protein association information are available, a weight function can be used to calculate the OS-score.

Laboratory Methods for Verifying Expression

Protein interactions can be validated using immunoprecipitation and immune complex assays. Antibodies which specifically bind a protein can be used to help identify other proteins to which that protein binds or with which it forms complexes. For example, the proteins in cultured cells can be metabolically labeled with 35S-methionine and then lysed under non-denaturing conditions. The cell lysate is incubated with antibodies and immunoprecipitated with a solid phase matrix that binds the antigen-antibody complex. Proteins which associate or complex with other proteins to carry out some specific function are co-immunoprecipitated even when antibodies are specific for one protein. The proteins within the immune complexes can be analyzed for molecular size using SDS-PAGE and autoradiography and for enzymatic activity using enzymatic assays well known in the art.

QPCR is a method for quantifying a nucleic acid molecule based on detection of a fluorescent signal produced during PCR amplification (Gibson et al. (1996) Genome Res 6:995–1001; Heid et al. (1996) Genome Res 6:986–994). Amplification is carried out on machines such as the ABI PRISM 7700 detection system that consists of a 96-well thermal cycler connected to a laser and charge-coupled device (CCD) optics system. To perform QPCR, a PCR reaction is carried out in the presence of a doubly labeled "TAQMAN" probe. The probe, which is designed to anneal between the standard forward and reverse PCR primers, is labeled at the 5' end by a flourogenic reporter dye such as 6-carboxyfluorescein (6-FAM) and at the 3' end by a quencher molecule such as 6-carboxy-tetramethyl-rhodamine (TAMRA). As long as the probe is intact, the 3' quencher extinguishes fluorescence by the 5' reporter. However, during each primer extension cycle, the annealed probe is degraded as a result of the intrinsic 5' to 3' nuclease activity of Taq polymerase (Holland et al. (1991) Proc Natl Acad Sci 88:7276–7280). This degradation separates the reporter from the quencher, and fluorescence is detected every few seconds by the CCD. The higher the starting copy number of the nucleic acid, the sooner a significant increase in fluorescence is observed. A cycle threshold (CT) value, representing the cycle number at which the PCR product crosses a fixed threshold of detection is determined by the instrument software. The CT is inversely proportional to the copy number of the template and can therefore be used to calculate either the relative or absolute initial concentration of the nucleic acid molecule in the sample. The relative concentration of two different molecules can be calculated by determining their respective CT values (comparative CT method). Alternatively, the absolute concentration of the nucleic acid molecule can be calculated by constructing a standard curve using a housekeeping molecule of known concentration. The process of calculating CTs, preparing a standard curve, and determining starting copy number is performed by the SEQUENCE DETECTOR 1.7 software (ABI).

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co transform competent yeast EGY48[p8op-lacZ] cells using a polyethylene glycol/lithium acetate protocol. Transformed yeast cells are plated on synthetic dropout (SD) media lacking histidine (His), tryptophan (-Trp), and uracil (-Ura), and incubated at 30 C. until the colonies have grown up and are counted. The colonies are pooled in a minimal volume of 1×TE (pH 7.5), replated on SD/-His/Leu/-Trp/-Ura media supplemented with 2% galactose (Gal), 1% raffinose (Raf), and 80 mg/ml 5 bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C. until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

In an alternative to a yeast two hybrid system analysis of proteins, an antibody array can be used to study direct protein interactions and phosphorylation. A variety of protein ligands are immobilized on a membrane using methods well known in the art. The array is incubated in the presence of cell lysate until protein:antibody complexes are formed. Proteins of interest are identified by exposing the membrane to an antibody specific to the protein of interest. In the alternative, a protein of interest is labeled with digoxigenin (DIG) and exposed to the membrane; then the membrane is exposed to anti-DIG antibody which reveals where the protein of interest forms a complex. The identity of the proteins with which the protein of interest interacts is determined by the position of the protein of interest on the membrane.

Antibody arrays can also be used for high-throughput screening of recombinant antibodies. Bacteria containing antibody genes are robotically-picked and gridded at high density (up to 18,342 different double-spotted clones) on a filter. Up to 15 antigens at a time are used to screen for clones to identify those that express binding antibody fragments. These antibody arrays can also be used to identify proteins which are differentially expressed in samples (de Wildt et al. (2000) Nature Biotechnol 18:989–94).

EXAMPLES

I. SLIPR for Pathway Curation

Semi-Linear Pathway Representation (SLIPR) was used to compare pathways in a linear fashion. Two-dimensional (2-D) diagrams of pathways were transformed into a one-dimensional (1D) format. 2-D diagrams are designated graph pathways, and their component 1-D pathways are designated linear pathways. One graph pathway can be transformed into multiple linear pathways. The generation of graph pathways and their corresponding linear pathways is called pathway curation. Pathways were hand-curated by scientists with expertise in the relevant pathways. In addition to generating graph and linear pathways, the scientists produce a pathway description file for each pathway and protein files for all proteins in the pathways.

Chart of Symbols Describing Nodes and Modes of a Pathway

--> direct interaction with direction. Used for known direct interactions between two proteins
--| direct inhibition with direction. Used for direct inhibition between two proteins
-- association. Used when interaction is uncertain or indirect, can be based on co-expression.
== parallel members. Proteins that serve the same function, usually variants of one gene or members of the same family.
<> clear interaction, but direction equal or unknown; can indicate that more than one protein is necessary to carry out the interaction.
** bifurcating members, usually appears only at the beginning or ending of a pathway. When it occurs in the middle of a pathway, it usually predicts a feedback loop
( ) indicates an atom or small molecule present. If the small molecule is unknown, it can be omitted, but if it is known, its name should appear between the parentheses (e.g. (Ca)) as shown below.
[ ] involving another pathway. The pathway name or id should appear within the bracket.
++ indicates the coupling of at least two molecules to form a functional node in a pathway. SLIPR examples are shown below:

All atoms or small molecules are included inside a set of parentheses.

$A1 \rightarrow (Ca) \rightarrow A1 \rightarrow (Cytidine_{13} \: Diphosphate_{13} \: Choline)$.

If there are bifurcations or links to other pathways, the pathways appear inside a bracket.

$A1 \rightarrow [Ca_{13} \: triggered\_path1], A1 \rightarrow [Gs_{13} \: pathway]$.

If a pathway bifurcates in the middle or at the end, **[path_name] is used to record this.

$A \rightarrow B \rightarrow (xx) \rightarrow C \rightarrow D[New\_path1] \rightarrow E \: [New_{13} \: path_{13} \: 2]$.

If more then one bifurcation occurs at a single point, $D \rightarrow **[New\_path1]==[New_{13} \: path2]$ is used. New_path1 and new$_{13}$ path2 are shown elsewhere.

If a bifurcation occurs to the left side of a pathway, $[Prev\_path1] \rightarrow A \rightarrow B \sim xx \sim C$ is used. There should be two files: an amino acid file, and a pathway specification file. If the root_name is cardio, the two files should be cardio.aa and cardio.pw.

If a pathway name, gene name, or curator is designated by more than one word, an underscore should be used to fill the space between them. For example, thyroid receptor would have been entered as thyroid$_{13}$ receptor.

FASTA Format for Pathway and Protein Entries

The pathway was entered in a FASTA-like format, with the first line containing >Pw$_{13}$ id, Pw_name, Pw_annotation, Source, Curator, Date, [species] as shown below:

$Pr1 \rightarrow Pr2 -- Pr3 == Pr4  Pr5  Pr6$

No spaces have been used in entering the data, and each line contains up to a fixed number of characters, where:

Pw$_{13}$ id: Genmetrics$_{13}$ id for the pathway.
Pw_name: A name for the pathway, with species designated as a three letter abbreviation. (GPCR$_{13}$ hum)
Pw_annotation: A brief description of the function of the pathway
Source: Designated database, i.e., KEGG, or user name
Curator: The person who worked on and submitted the pathway to the database.
Date: Date of curation.

For protein entries, the following FASTA format was used: >Pr$_{13}$ id, Pr_name, Pr$_{13}$ annotation, Source, Curator, Date, [species] as shown below:

ABCDEFG

No spaces have been used in entering the data, and each line contains up to a fixed number of characters, where:

Pr$_{13}$ id: Any id from a defined source (such as SWISSProt$_{13}$ id)
Pr_name: A short name for a protein, with species designated as a three letter abbreviation (gpcr$_{13}$ hum).
Pr_annotation: Annotation for the protein
Source: Database such as SwissProt$_{13}$ id, GenBank$_{13}$ id, EMBL$_{13}$ id, DDBJ$_{13}$ id, etc.
Curator: The person who discovered or worked on the protein or its encoding gene (person, laboratory, or organization)

II. PMsearch Documentation

PMsearch is the name applied to a pathways search that uses the algorithms and programs described herein to compare pathways using the information in the pathways database (db.pw) and protein sequence (db.aa) files. After a user specifies a query pathway and a search database, PMsearch compares the query pathway with each pathway in the database. The query pathway was specified by two input files: a query.pw, pathway file, and a query.aa, the protein sequence file. The query.pw contained pathway information, in PASTA-like format, and the query.aa contained the protein sequences in FASTA format. Once a search had been submitted, pm_search performed the search and reported as alignments all homologous or orthologous pathways that exceeded a user-specified threshold. The user can specify other parameters as presented in the Genmetrics User Manual (2001; Genmetrics, San Jose Calif.)

The alignment showed the identity between two sequences or non-protein molecules such as the atoms, side groups, vitamins, cofactors, carbohydrates, proteins, nucleotides, and the like. A linear pathway would have been represented by the sequences of the proteins involved.

In more detail: if $a_i$ are the elements of sequence a and $b_j$ are the elements of sequence b, an alignment is a set of pairs $\{(a_{i(t)}, b_{j(t)}), t=1 \ldots k\}$ where the sequences i(t) and j(t) are increasing where increasing i(t) and j(t) means that the elements of the sequences are always in the same order.

Each alignment has been assigned a score based on acceptable matches minus penalties assessed for gaps and their lengths. The scores allowed PMsearch to rate similarities between pathways that estimate evolutionary relatedness. For example, given the following sequences, UIPQWEFOIUTFJLK and PQEFOIABCDFJ, a good alignment might be:

```
UIPQWXEFOI---UFJLK
 ||  |||   ||
   PQ--EFOIABCDFJQRS
```

In a pathway alignment, the proteins do not have to be identical, but they must be homologous as shown below.

Outside of the alignment region, it does not matter whether all of the letters match. A one-sided gap, like "WX" only has non-matching elements on one side. However, the alignment below has a two-sided gap which could be written:

```
OI---UFJ              OI----UFJ
 ||   ||      or       ||    ||
OIABCDFJ              OIABCD-FJ
``` where the two-sided gap (U does not match ABCD, three spaces in the first sequence) is replaced by two one-sided gaps (four spaces in the first sequence, followed by one space in the second). In this case, spacing was recognized by the algorithm which enumerated two one-sided gaps.

Then, given the alignment z, the score is given by $$S_z(a,b) = \sum_{t=1}^{k} s(a_{i(t)}, b_{j(t)}) - n_{gap}\Delta - l_{gap}\delta$$

where $s(x,y)$ is the similarity of protein x and protein y, $n_{gap}$ is the number of gaps in z, $l_{gap}$ is the total length of the gaps, $\Delta$ is a parameter called the Agap opening@ penalty, and $\delta$ is a second parameter called the Agap extension@ penalty. It should be noted that more than one alignment is always possible for any two sequences and that different alignments can have different scores.

PMsearch uses the optimization algorithm to find the alignment with the highest score by computing and comparing optimal subalignments. If the optimal alignment includes the matching pair (p,q), then the subalignment of $\{a_1, Y, a_p\}$ to $\{b_1, Y, b_q\}$ must itself be optimal for those sequences. Otherwise, changing to the correct, optimal alignment of $\{a_1, Y, a_p\}$ to $\{b_1, Y, b_q\}$ would increase the score of the whole alignment of a to b.

For the alignment to get to (m, n), it must go through one of:

(m−1, n−1) (in which case $a_m$ and $b_n$ are a match),
(m−1, n) (meaning (m,n) is in a gap in sequence 2), or

|    | a1      | a2      | a3      | a4      |
|----|---------|---------|---------|---------|
| b1 | s(1, 1) | s(2, 1) | s(3, 1) | s(4, 1) |
| b2 | s(1, 2) | s(2, 2) | s(3, 2) | s(4, 2) |
| b3 | s(1, 3) | s(2, 3) | s(3, 3) | s(4, 3) |

In detail, the alignment algorithm is

For i=1 to m
For j=1 to n $H(i,j) = \max \{H(i-1, j-1) + s(i,j), H_h(ij), H_v(i,j)\}$, where $H_h(i,j) = \max \{H_h(i, j-1) - \delta, H(i, j-1) - \delta - \Delta\}$ $H_v(i,j) = \max \{H_v(i-1, j) - \delta, H(i-1, j) - \delta - \Delta\}$ End Here $H(i,j)$ is the score for the subalignment $\{a_1, Y, a_i\}$ to $\{b_1, Y, b_j\}$ assuming that $(a_i, b_j)$ are paired; $H_h(i,j)$ is the score if (i,j) is in a horizontal gap; $H_v(i,j)$ is the score if (i,j) is in a vertical gap. (Assume $H(i,0) = H(0,j) = 0$ for all i,j, as boundary conditions.)

A procedure called traceback was used to finish the alignment. From the last matched position, it is necessary to literally trace back and determine whether H, $H_h$, or $H_v$ was used. At each point in the alignment, the algorithm determined whether the previous point was diagonally before (no gap), horizontally before (gap in first sequence) or vertically before (gap in second sequence).

Such an algorithm can be extended to compare two pathways involving mode information, where modes are non-protein small molecules. The similarity between any mode and node is zero; the similarity between two modes can be based on identity mapping, meaning the similarity is 1 for two identical non-protein molecules, and 0 if the molecules are different. Alternatively, the user can specify the use of a similarity matrix based on properties such as structural similarity. The comparison can be made at the node level, mode level, or combined mode and node level with a weighting coefficient K. When PM_search is typed without argument, the screen displays:

Usage: pm_search <Path_DB> <Query_Path> [A=#] [B=#]
 [E=#] [R=#] [S=#] [GI=#] [GE=#]
Path_DB: pathway database name
Path_DB.p
Path_DB.aa—amino-acid sequences file
Query_Path: Query pathway
Query_Path.pw—your query pathway file
Query_Path.aa—amino-acid sequences file for the query
A=#: coefficient for node and mode weight, default A=1
B=#: max number of alignment to show, default 200
V=#: max number of 1-line summary to show, default 200
R=#: Report all hits above score, default 20
GI=#: gap penalty for initiating a gap, default: 5
GE=#: gap penalty for extending a gap, default: 2
E=#: Expect value as a cutoff, default, not used
S=#: BLASTP score used for finding hits, default 100.

PMsearch Sample Output

Sample output from PMsearch is shown below. The query was a pathway taken from KEGG (hsa00625, Tetrachloroethene degradation pathway). The database searched was keggall, a pathway database released from KEGG. This particular search was node-only.

```
PMsearch 0.1 Path Metrics [Sep. 20, 2001]
[Build linux x-86 Jul. 30, 1998]
Query= hsa00625 (5 proteins)
PW Database= keggall
(4,881 pathways; 71,600 total proteins).
 Pathways with above-threshold alignments:    Score
hsa00625    Tetrachloroethene degradation      100
hsa00360    Phenylalanine metabolism            59
hsa00120    Bile acid biosynthesis              58
hsa00627    1,4-Dichlorobenzene degradation     40
hsa00100    Sterol biosynthesis                 40
>hsa00625   Tetrachloroethene degradation
Query:   1   hsa:51144 hsa:2052 hsa:2053 hsa:51004  4
%_id:         |1.00|    |1.00|   |1.00|    |1.00|
Sbjct:   1   hsa:51144 hsa:2052 hsa:2053 hsa:51004  4
Query:   5   hsa:9420    5
%_id:         |1.00|
Sbjct:   5   hsa:9420    5
>hsa00360   Phenylalanine metabolism
Query:   4   hsa:51004 hsa:9420    5
```

```
                        -continued
%_id:                |1.00|    |1.00|
Sbjct:      24  hsa:51004 hsa:9420   25
>hsa00120    Bile acid biosynthesis
Query:       4  hsa:51004 hsa:9420    5
%_id:                |1.00|    |1.00|
Sbjct:      22  hsa:51004 hsa:9420   23
>hsa00627    1,4-Dichlorobenzene degradation
Query:       4  hsa:51004 hsa:9420    5
%_id:                |1.00|    |1.00|
Sbjct:       1  hsa:51004 hsa:9420    2
>hsa00100    Sterol biosynthesis
Query:       4  hsa:51004 hsa:9420    5
%_id:                |1.00|    |1.00|
Sbjct:      12  hsa:51004 hsa:9420   13
```

III PMortholog Documentation

PMortholog is an ortholog prediction program for use with the pathways database. For a given pathway, specified by query.pw and query.aa files and a given protein database involving one or more species, the program reported all predicted orthologous pathways. Orthologous predictions were most accurate for evolutionarily related species. Less than optimal results were reported if two species were evolutionarily distant or if multiple pathways existed.

The output is displayed on the screen for all the species within the protein database where an alignment above the user-specified or default threshold was detected. The results were listed in the order of OS scores. An exact match between two proteins resulted in a score of 20; and for inexact matches between the aligned proteins, the score is percent_identity*20, where percent_identity was the overall identity between two protein using a Smith-Waterman alignment.

When PM_ortholog is typed without argument, the screen displays:

Usage: pm_ortholog <query_pw> <query_aa> <protein_db> [A=#] [B=#] [E=#] [R=#] [S=#] [GI=#] [GE=#]
Query_Path: Query pathway
Query_Path.pw—your query pathway file
Query_Path.aa—amino-acid sequences file for the query
protein_db: protein database in FASTA format for the concerned species
A=#: coefficient for node and mode weight, default A=1
B=#: max number of alignment to show, default 200
V=#: max number of 1-line summary to show, default 200
R=#: cutoff score to report, default 20
GI=#: gap penalty for initiating a gap, default: 5
GE=#: gap penalty for extending a gap, default: 2
E=#: Expect value as a cutoff, default, not used
S=#: BLASTP score used for finding hits, default 100.

PMortholog Sample Output

Sample output from PMortholog is shown below. The query is hsa00625, the same query used to run PMsearch. The protein database used for the prediction was Genpept124.

```
Ortholog Prediction Results
Query_path:
hsa00625           Tetrachloroethene degradation      Homo sapiens
hsa:51144     hsa:2052     hsa:2053     hsa:51004     hsa:9420

PM_ORTHOLOG 0.1, Pathmetrics, Inc. [Oct. 20, 2001] [Build linux-x86]
Query pathway= hsa00625 (5 proteins)
Database: /u1/pub_db/sp_db/allspecies.aa (374855 proteins)
Summary of ortholog pathways:
   Hit_nu   species                                 score
-----------------------------------------------------------------------
       1:   Homo sapiens                 .........  100.00
       2:   Mus musculus                 .........   65.20
       3:   Rattus norvegicus            .........   65.20
       4:   Caenorhabditis elegans       .........   44.20
       5:   Drosophila melanogaster      .........   37.80
       6:   Arabidopsis thaliana         .........   37.00
>Hit 1: Ortholog pathway for:   Homo sapiens. With score: 100.00
Query:   hsa:51144     hsa:2052     hsa:2053     hsa:51004     hsa:9420
%_id:    |1.00|        |1.00|       |1.00|       |1.00|        |1.00|
Sbjct:   gi15082281    gi13097729   gi181395     gi4680659     gi13094303

>Hit 2: Ortholog pathway for:   Mus musculus. With score: 65.20
Query:   hsa:51144     hsa:2052     hsa:2053     hsa:51004     hsa:9420
%_id:    |0.85|        |0.88|       |0.81|       |0|           |0.72|
Sbjct:   gi3142702     gi12857870   gi12832382   - - -         gi12850151

>Hit 3: Ortholog pathway for:   Rattus norvegicus. With score: 65.20
Query:   hsa:51144     hsa:2052     hsa:2053     hsa:51004     hsa:9420
%_id:    |0.81|        |0.88|       |0.84|       |0|           |0.73|
Sbjct:   gi4098957     gi207689     gi55930      - - -         gi1226240

>Hit 4: Ortholog pathway for:   Caenorhabditis elegans. With score: 44.20
Query:   hsa:51144     hsa:2052     hsa:2053     hsa:51004     hsa:9420
%_id:    |0.48|        |0.56|       |0.42|       |0.44|        |0.31|
Sbjct:   gi726418      gi1465805    gi3876864    gi2088820     gi13775482

>Hit 5: Ortholog pathway for:   Drosophila melanogaster. With score: 37.80
Query:   hsa:51144     hsa:2052     hsa:2053     hsa:51004     hsa:9420
%_id:    |0.48|        |0.48|       |0.20|       |0.47|        |0.26|
Sbjct:   gi7290849     gi7302538    gi7290805    gi7296986     gi7304256
```

```
>Hit 6:  Ortholog pathway for:      Arabidopsis thaliana. With score: 37.00
Query:   hsa:51144    hsa:2052      hsa:2053       hsa:51004      hsa:9420
%_id:    |0.48|       |0.21|        |0.42|         |0.40|         |0.34|
Sbjct:   gi13605726   gi13374854    gi1109600      gi11994239     gi9502380
```

IV. PMpredict

PMpredict has the ability to predict multiple novel pathways that are homologous to a query pathway. The query was a pathway involving query.pw and query.aa files and the databases searched were a protein database and a protein-protein association database obtained from microarray data or from counting clones in cDNA libraries of dbEST.

Results were predicted pathways with homology to the query pathway, alignments showed the similarities between nodes and the association coefficient between nodes. Deletions were allowed, and undetected, unsupported, or unneeded pathway members, i.e., no proteins in the db.aa file, no expression in the db.ex file, or changed biological function, were deleted. Optimal predicted pathways were reported first, followed by suboptimal predicted pathways (which have one or two altered proteins).

When PM_predict is typed without argument, the screen displays:
Usage: pm_predict <Expr_DB> <Query_Path> [A=#] [B=#] [E=#] [R=#] [S=#] [GI=#] [GE=#]
Expr_DB: expression database name Expr_DB.ex—gene-to-library expression file Expr_DB.aa—amino-acid sequences file
Query_Path: Query pathway Query_Path.pw—your query pathway file Query_Path.aa—amino-acid sequences file for the query
A=#: coefficient for node and mode weight, default A=1
B=#: max number of alignment to show, default 200
V=#: max number of 1-line summary to show, default 200
R=#: cutoff score to report, default 20
GI=#: gap penalty for initiating a gap, default: 5
GE=#: gap penalty for extending a gap, default: 2
E=#: Expect value as a cutoff, default, not used
S=#: BLASTP score used for finding hits, default 100.

Dynamic Programming Method

Let GPW denotes a given pathway with J nodes, $p_1, p_2, \ldots, p_J$. For each $p_i$, $1<=i<=J$, we can get a set $A_i=\{a_{ij}: 0<=j<=n_i\}$ by a similarity search, for example, using FASTA or BLAST, where the similarity measure between $p_i$ and $a_{ij}$ is denoted by $S_{ij}$. In the case $n_i=0$, i.e., $A_i$ is empty, we set $a_{ij}=-D$ ($D>=0$) and $n_i=1$ to allow for a deletion. Let $C_{ik,jl}$, $1<=i,j<=J$, $1<=k<=n_i$, $1<=l<=n_j$ denotes the co-expression coefficient between $a_{ik}$ and $a_{jl}$.

Dynamic programming is applied to predict the highest-scoring putative pathway and involves the following three steps: 1) initialization, 2) multiple array filling, 3) traceback. In the first step, a two dimensional array $M=M_{ij}$ with J rows and variant length for each row, the length for i-th row is $n_i$, is set up. Initially, $M_{ji}=0$, where $1<=i<=n_j$. Second, the array is filled using backward recursion:

$$M_{ik} = \max_{\substack{j>i \\ 1\le l\le n_j}} \{w(a_{ik}, a_{jl}) + M_{jl}\theta(w(a_{ik}, a_{jl}))\}$$

for $1 \le k \le n_i$, $1 \le i \le J$ where $\theta(.)$ is the step function defined as $\theta(v)=\{0, \text{ if } v<=0; 1, \text{ if } v>0\}$; and $w(.,.)$ is the scoring function between the two nodes, defined as:

$$w(a_{ik}, a_{jl}) = \begin{cases} 0, \text{ if } i = j, a_{ik} = a_{jl}, a_{ik} = -D, \text{ or } a_{jl} = -D \\ \theta(c_{ik,jl} - t_c) \cdot \{\alpha(1 - |s_{ik} - s_{jl}|) + (1 - \alpha)c_{ik,jl}\} \text{ otherwise.} \end{cases}$$

After filling the array, traceback is used to identify putative pathways $PPW_j$, $1<=j<=\max n_i$ with the top n best scores if possible. Sub-optimal candidate pathways can also be reported. For local good-score alignments, a minimum local threshold score can be defined. If the increase in score per step is less than this threshold score, the output only reports those segments of the pathway having an acceptable score.

PMpredict Sample Outputs

Output 1. Predicted Novel Pathways and Interactions Similar to EPO Pathway

Sample output from PMpredict is shown below. The query is the human erythropoeitin (EPO) response pathway that has been well characterized. The protein database was a *Homo sapiens* protein database extracted from the NCBI GBpri database (release 124). An expression profile was obtained for each GBpri sequence based on its corresponding UniGene expression profile as extracted from the 300 largest libraries in dbEST. Protein-protein association matrices were calculated using the program, calc_assoc. Expression data was used in a binary fashion, i.e. if a gene was seen in a specific library, it was scored 1, otherwise, zero. No quantitative data was used in this computation, and D was set to zero in this prediction.

```
PM_PREDICT 0.1, Pathmetrics, Inc. [Oct. 20, 2001] [Build linux-x86]
Query pathway= EPO (17 proteins)
Database:   /u1/pub_db/Tom.aa
            15,903 proteins.
Summary of predicted pathways:
Putative_pathway_ID           status              score
-----------------------------------------------------------------
   putative_pw_1              optimal             100.80
   putative_pw_2              optimal              17.95
   putative_pw_3              optimal              12.80
   putative_pw_4              sub-optimal         100.30
   putative_pw_5              sub-optimal          99.85
```

-continued

```
>putative_pw_1    Optimal predicted pathway with score:    100.80
Query:    1  gi14348285   1       gi8169051    1       gi14741745    1        3
%_id:                                                    |0.14|
Sbjct:    0  - - -        - - - - - -          - - -    Hs.85844      0.66     1

Query:    4  gi13560998   1       gi736683     1       gi36454       1        6
%_id:        |0.16|               |0.18|                |0.10|
Sbjct:    2  Hs.119257    0.66    Hs.7844      0.55    Hs.306088     0.56     4

Query:    7  gi181976     1       gi6164601    1       gi190910      1        9
%_id:        |0.11|               |0.79|                |0.99|
Sbjct:    5  Hs.66392     0.49    Hs.326392    0.64    Hs.184050     0.58     7

Query:    10 gi496091     1       gi177994     1       gi181155      1        12
%_id:        |0.99|               |1.00|                |0.99|
Sbjct:    8  Hs.85181     0.69    Hs.155140    0.55    Hs.165843     0.33     10

Query:    13 gi187517     1       gi13548677   1       gi4126584     1        15
%_id:        |0.34|               |0.33|                |0.28|
Sbjct:    11 Hs.94576     0.29    Hs.171695    0.64    Hs.306117     0.74     13

Query:    16 gi182735     16
%_id:        |0.17|
Sbjct:    14 Hs.149923    14

>putative_pw_2    Optimal predicted pathway with score:    17.95
Query:    10 gi496091     1       gi177994     1       gi181155      1        12
%_id:                             |0.31|
Sbjct:    0  - - -        - - -   Hs.307357    0.17    - - -         - - -    1

Query:    13 gi187517     1       gi13548677   1       gi4126584     1        15
%_id:                                                  |0.14|
Sbjct:    1  - - -        - - - - - -          - - -   Hs.192861     0.20     2

Query:    16 gi182735     16
%_id:        |0.11|
Sbjct:    3  Hs.250692    3
```

Information derived from output 1: The erythropoietin (EPO) response pathway regulates the amount of oxygen in the blood by increasing the number of circulating red blood cells (RBC). EPO mediates this response by binding to the EPO receptor which transduces a signal through a pathway of 17 proteins which are shown in the table below:

| GenPept ID | Protein pathway: function (Homo sapiens) |
|---|---|
| gi14348285 | EPO, the hormone that regulates erythrocyte differentiation and maintains the number of circulating RBC to determine the amount of oxygen in the blood; EPO receptor ligand |
| gi8169051 | EPO Receptor, a member of the cytokine family of receptors, functions in EPO-induced erythroblast proliferation and differentiation, induces signal transduction through JAK-STAT |
| gi14741745 | JAK2, a tyrosine kinase of the non-receptor type, functions in interleukin 2 and interleukin 3 induced signal transduction through JAK-STAT, also regulates the cell cycle, apoptosis and the cytoskeleton, also activated by interferon-gamma and growth hormone |
| gi13560998 | PLC gamma, a phospholipase that is a major substrate for heparin-binding growth factor 1-activated tyrosine kinase, involved in intracellular calcium signaling, |
| gi736683 | STAT5, a member of the STAT (signal transducer and activator of transcription) family of transcription factors, activated by IL-2 and IL-5, mediates JAK kinase transduction of signals from cytokines, growth factors and hormones, |
| gi6164601 | SOS1, (son of sevenless) a guanine nucleotide exchange factor that promotes the exchange of Ras-bound GDP by GTP, interacts with GRB2; the molecular complex consisting of GRB2 and SOS1 couples receptor tyrosine kinases to Ras signaling |
| gi190910 | Ras, a member of the small GTPase superfamily, involved in MAPK activation and cell proliferation; Ras mutations are involved in tumor formation |
| gi496091 | RAF, a serine-threonine kinase involved in the transduction of mitogenic signals from the cell membrane to the nucleus, part of the Ras-dependent signaling pathway from receptors to the nucleus, involved in regulating apoptosis; corresponding oncogene is implicated in radiation-resistant laryngeal cancer in humans |
| gi187517 | MEK (phosducin), soluble phosphoprotein which may regulate visual phototransduction or photoreception, forms a complex with beta and gamma subunits of the GTP-binding protein, transducin |
| gi13548677 | MAPK phosphatase-7, a member of the non-receptor family of tyrosine phosphatases, inactivates mitogen-activated protein kinase by dephosphorylation |
| gi4126584 | ELK1, a transcription factor that is a member of the Ets family; progression of some tumors has been associated with rearrangements of the ELK1 gene |
| gi182735 | c-fos, a nuclear phosphoprotein and transcription factor that forms heterodimers with c-Jun and stimulates transcription of genes containing activator protein (AP-1) regulatory elements, involved in the development of the skeleton and has a major role in signal transduction, cell proliferation and differentiation. |
| gi177994 | CKII-alpha, casein kinase II alpha subunit, a serine-threonine kinase with broad specificity, has a role in cell growth and proliferation, and may be involved in cell adhesion, the response to DNA damage, and mammary gland tumorigenesis |
| gi181155 | CKII-beta, casein kinase II beta subunit, regulates the basal activity of the casein kinase II alpha subunit, involved in regulating cell growth and differentiation |

-continued

| GenPept ID | Protein pathway: function (Homo sapiens) |
|---|---|
| gi386839 | JUN, a transcription factor that interacts with c-fos to form the heterodimer AP-1 complex, involved in apoptosis; associated with the diseases retinitis pigmentosa, renal cell carinoma and IgA nephropathy |
| gi6454 | SHC transforming protein [Homo sapiens], couples activated growth factor receptors to a signaling pathway that regulates the proliferation of mammalian cells |
| gi181976 | GRB2, an adaptor protein containing SH2 and SH3 domains that associates with receptor tyrosine kinases, forming a GRB2/ras complex, resulting in a mitogenic response |

The PMpredict function allowed the following types of questions to be asked:

1) Does the query pathway predict a pathway(s) which is similar or distinct in function?
2) How many proteins are in the predicted pathway?
3) How many have been described in scientific literature by sequence, by activity or by protein-protein interactions? What is the function the predicted pathway member(s)?
4) Has the protein(s) previously been identified as a member(s) of the predicted pathway?

Specifically for the data from the EPO pathway, the questions are:

1) Are there other ligand receptors in humans co-expressed with members of the EPO pathway?
2) What other pathway(s) in humans is significantly related to the EPO pathway?
3) How many known or novel proteins (nodes) are in the predicted pathway compared to the 17 proteins in the EPO pathway?
4) How many protein-protein interactions (modes) are shared between query and predicted pathway? How many are distinct?

Using PMpredict with the EPO pathway as query, 14 nodes were predicted in putative_pw__1. The EPO pathway predicted the nerve growth factor (NGF) pathway. The tyrosine kinase, JAK2, had an association with the receptor tyrosine kinase, NTRK1 (Hs.85844). NTRK1 is the high affinity nerve growth factor (NGF) receptor which binds NGF, a neurotrophin. NTRKK1 has a role in the development and function of the nociceptive receptor and in thermal regulation via sweating. It is known in the scientific literature that NTRK1 signals through activation of ERK1 (extracellular signal-regulated kinase 1), by either the SHC or PLC-gamma-1 dependent signaling pathway. Therefore, pathway proteins for this pathway are PI-3-kinase, SHC and PLC gamma-1. PMpredict results were supported in that SHC and PLC gamma-1 are also members of the EPO pathway. In addition to these characterized protein-protein interactions, the predicted pathway contained 2 uncharacterized pathway modes involving EMS1 (carcinoma associated protein) and growth hormone inducible soluble protein. This implied that signal transduction of the EPO pathway has shared yet distinct pathway members with the NGF pathway. Both pathways regulate cell differentiation: The former affects erythrocytes while the latter regulates neuron activity.

Expression levels of the cDNAs which correspond to interacting pathway members ranged from 0.29 to 0.74 (high correlation is 0.99). The score was derived by the dynamic programming and was based on counting clones present in the dbEST database. The abundance of the cDNAs found within this pathway was highest between ELK1 and c-fos. ELK1 and c-fos are transcription factors that are found in the nucleus. Published reports on tissue specificity reported ELK1 transcripts in lung and testis, while c-fos was expressed in numerous tissues including lung. This experimental data supported the expression correlation produced using dynamic programming for ELK1 and c-fos.

```
Output 2. Predicted interacting segments homolo-
         gous to Tyrosine metabolism pathway
Query pathway: hsa00350        Tyrosine metabolism
                               [Homo sapiens]
Entry taken from KEGG database. Protein and ex-
pression databases used are the same as Ex.1.
Segment I,  scores: S_total=31.8; S_mean=6.36.
Query: hsa:218    1    hsa:220    1    hsa:221
%_id:      0.74            0.76             0.60
Sbjct: Hs.159608  0.54 Hs.76392  0.54 Hs.159608

Segment II, scores: S_total=24.0; S_mean=6.0.
Query: hsa:2805   1    hsa:2806   1    hsa:1629
%_id:      0.57            0.56             0.32
Sbjct: Hs.250801  0.51 Hs.101067  0.44 Hs.75642   etc.
```

Information derived from output 2: The tyrosine metabolic pathway (hsa00350) has 73 nodes. The first pairwise result, Segment I, predicts two homologous proteins that belong to different pathways. Aldehyde dehydrogenase (hsa:218) plays a major role in the detoxification of alcohol-derived acetaldehyde and preferentially oxidizes aromatic aldehyde substrates. It is co-expressed with fatty aldehyde dehydrogenase (Hs.159608) which catalyzes the oxidation of long-chain aliphatic aldehydes. Both proteins belong to the family of aldehyde dehydrogenases, yet have distinct substrates and functions.

```
Output 3. Predicted interacting segments homolo-
         gous to aminosugars metabolism
Query pathway: hsa00530        Aminosugars metabolism
                               [Homo sapiens]
Entry taken from KEGG database. Protein and ex-
pression databases used are the same as Eg.1.
Segment I.  scores: S_total=54.5; S_mean=7.79.
Query: hsa:10007  1    hsa:3073   1    hsa:3074   1
%_id:      1.00            1.00             1.00
Sbjct: Hs.118625  0.52 Hs.198427  0.58 Hs.118625  0.35
Query: hsa:10020
%_id:      1.00
Sbjct: Hs.5920

Segment II. scores: S_total=47.1; S_mean=6.73.
Query: hsa:2645   1    hsa:3098   1    hsa:3099   1
%_id:      0.60            0.74             0.74
Sbjct: Hs.118625  0.49 Hs.198427  0.49 Hs.118625  0.49
Query: hsa:3101
%_id:      0.58
Sbjct: Hs.198427  etc.
```

Information derived from output 3: The aminosugar metabolic pathway (hsa00530) has 22 nodes. The first pairwise result, Segment I, predicts glucosamine-6-phosphate isomerase is co-expressed with hexokinase. Hexokinases phosphorylate glucose to produce glucose-6-phosphate, thus committing glucose to the glycolytic pathway. Glucosamine-6-phosphate isomerase catalyzes the breakdown of glucosamine-6-phosphate to fructose 6-phosphate. The latter intermediate is converted to glucose-6-phosphate by phosphohexose isomerase. Both hexokinase and glucosamine-6-phosphate isomerase generate intermediates for glycolysis. This example illustrates the co-expression of proteins that converge from the aminosugar metabolic pathway and the glycolytic pathway.

Constrained Clustering Method

An alternative method for predicting novel pathways homologous to a known pathway uses "constrained clustering". In this case, proteins for the novel pathway were found using a clustering algorithm which has specific constraints. The constraints guaranteed that: 1) the predicted pathway has only one protein for each node of the query; and 2) known interactions take precedence in the pathway, overwriting any pathway component based solely on protein-protein association data. The inputs are: 1) new proteins: proteins of undetermined function and their protein-protein association data, and 2) a query pathway that serves as a template for predicting novel pathways.

First, similarities were computed for every new protein versus every query protein. New proteins were discarded if they had no similarity to a query protein. The remaining new proteins were classified according to similarity. For example, a query of three proteins produced the following alignment matrix:

| $p_1$ | $p_2$ | $p_3$ |
|---|---|---|
| $h_{11}$ | $h_{21}$ | $h_{31}$ |
| ... | ... | ... |
| $h_{1m}$ | $h_{2n}$ | $h_{3k}$ | where $p_1$, $p_2$, $p_3$ are proteins in the query pathway, and $h_{11}, \ldots h_{1m}$ are proteins homologous to $p_1$ in whatever metric of interest to user; $h_{21}, \ldots h_{2n}$ homologous to $p_2$; and $h_{31}, \ldots h_{3k}$ homologous to $p_3$.

One constraint on the clustering was that proteins from the same column cannot be clustered together. In practical terms, this was implemented by assigning infinite distance to any pair of proteins that were in the same column. When a protein appeared in two different columns and had nearly the same degree of similarity to a protein in each column; the protein was tested separately in each column.

Pairwise distances were computed for clustering unless the proteins were in the same column. Otherwise, the distance was a function of similarity to query protein ($s_i$ and $s_j$), where i, j represented positions in the query pathway, and of protein-protein association ($a_{ij}$). Specifically, the relationship was $$d_{ij} = \alpha(1-a_{ij}) + (1-\alpha)|s_i - S_j|,$$

where α was a tuning parameter.

Different clustering algorithms were used, and they were distinguished by how distances, or linkage, between clusters were computed: 1) complete linkage indicated that the distance between clusters was equal to the maximum distance between proteins in the clusters; 2) single linkage indicated that the distance was the minimum distance between proteins; and 3) mean linkage indicated that the distance was a weighted average of the distances. Mean linkage was a special case of $l_p$-linkage, in which distances were combined by a weighted average of powers:

$$d_{new}^p = \frac{n_1 d_1^p + n_2 d_2^p}{n_1 + n_2} (p \geq 1)$$

(mean linkage is when $p = 1$).

For the constraint of known protein interactions, where two proteins were known to be present in the same pathway, $d_{ij}=0$ was assigned. V Web-interface Introduction A web-interface was constructed which has buttons linked to all software products and specifically includes pathway input, pathway search, pathway comparison, orthologous pathway prediction, and novel pathway prediction. Each button in the top menu of the web-interface is explained below.

Pathway Input

The button on the web-interface for submitting pathways into the existing pathways database is the input button. When submitting pathways, the user should follow the "SLIPR" standard. A pathway can be submitted using any symbol that is specified in "SLIPPIR". The gene_id has to be found in the existing protein database, or an error message appears. For example, when b0823==b2935>b4160b0350b0662 is submitted, the screen will show a message that input is complete. If one of the ids, b0350 was changed to B350, an error message reported that this id is not in the pathways database.

If a user is uncertain about whether a gene_id is correct, the user can use the function "Search gene by id". If the user typed aq_056 and clicked search, the computer reported the complete FASTA entry from the protein database with annotations for the encoded gene in the first line.

If a user only remembers the keywords for a gene, but not its exact ids, a helper can be used to find the gene id. For example, if the user typed the words, oxidase and glycolate, case-insensitive, and clicked submit, the computer will return all the proteins containing the keywords.

Retrieve Pathway

Retrieve pathway is used to retrieve pathways that exist in the pathways database. The pathway can be searched by Pathway_id, by gene_id, or by keywords. The pathway_ids follow the convention: the first three letters designate the species, and the last 5 digits denote the number of pathways in that species. Typing in hsa00625 and clicking submit returns the individual pathway. On the pathway, there are several active links which allow the user to see the pathway diagram which contains all the individual proteins. Typing in gene_id and clicking search will return with a list of all the pathways that contain that id. Boolean logic can be used to input the protein ids: DPD2_human (SwissProt id) or 5425 (KEGG id) for the same gene, Dpys_human (SwissProt id) or 1807 (KEGG id) for the same gene. Both SwissProt and KEGG ids are supported, and they are linked to the same non-redundant entry in the database. The pathways database can also be searched by keywords that occur in the annotation for the pathway.

Pathway Search

The function of this button is to perform pathway comparisons. The user should specify a query pathway. He can then compare this pathway against other pathways in our pathway databases. There are two ways to specify a query pathway: either by a pathway id, or by user input files. In the case of by pathway id, one should specify a pathway id and select a database in which this pathway id appears. In the second case, the user should input two files for his query pathway: (1) Query.pw: file containing the pathway for the query in FASTA format. (2) Query.aa: file containing all the protein sequences in the query.pw file in FASTA format. Try: hsa00625 (pathway involving 5 proteins, and it is a drug target pathway). The output shows the homologous pathways the search engine detected in our database. Since those pathways are from our database, the first alignment in the output is always the query. The other alignments in the output are homologous pathways presented in order of their OS score.

Ortholog Pathway

The ortholog button is used to query a known pathway in a given species against other species. The user specifies a query pathway and the program, PMortholog, produces the mostly likely corresponding pathway in another species. The query pathway is either a known pathway from the pathways database or is specified by the user query.pw and query.aa files. The species of interest against which PMortholog will search is specified by the user, or the user can specify "all" for all species in the pathways database Pathway Prediction PMpredict predicts novel pathways using a query pathway and a protein-protein association matrix. The protein-protein association matrix is derived from expression data. The user can specify a query pathway or submit query.pw and query.aa files. In the output, predicted novel pathways are listed in order of their OP scores. All optimal and suboptimal predictions above the user-specified threshold are reported. Sub-optimal predictions have a slightly lower score, but are as likely to represent the biological pathway. The sub-optimal pathways have more allowance for differences in signal intensity and scatter that can occur in different microarray experiments.

What is claimed is:

1. A computerized storage and retrieval system of biological information comprising:
   a means for entering data;
   a means for displaying the data;
   a programmable central processing unit programmed to perform automated analysis using semi-linear pathway representation (SLIPR) to compare and predict pathways and their components and to establish a pathways database;
   a means for storing data; and
   a relational database containing annotated and curated pathways and information on the pathways and their components.

2. The system of claim 1, wherein the information pertaining to the pathways and their components and stored in a plurality of tables further comprises proteins, their sequences and attributes; protein interactions; protein-protein associations; protein pathways; mRNA, microarray, and protein expression data; genes, their sequences and attributes; descriptions of cells, tissues, and organs; pathology reports; patient histories and treatments.

3. The system of claim 1, wherein the central processing unit is further programmed to run an algorithm or a method for constrained clustering or an optimization algorithm for dynamic programming and one or more functions or standard methods selected from retrieve, input, edit, annotate, search, calculate similarities, align, compare, optimize using linear next-neighbor criteria or global minimization criteria, and predict homologous or orthologous pathways and their components and, wherein the method for constrained clustering is further selected from average linkage, single linkage, complete linkage, K-means, or self-organizing maps.

4. The system of claim 3, wherein the central processing unit runs the optimization algorithm for dynamic programming further comprising:

a) initializing an array, in which a two dimensional array $M=M_{ij}$ with J rows and variant length for each row, the length for i-th row is $n_i$ is set up and $M_{ji}=0$, where $1<=i<=n_j$, b) backfilling the array via backward recursion with the formula $$M_{ik} = \max_{\substack{j>i \\ 1\leq l \leq n_j}} \{w(a_{ik}, a_{jl}) + M_{jl}\theta(w(a_{ik}, a_{jl}))\}$$

for $1 \leq k \leq n_i, 1 \leq i \leq J$ where $\grave{e}(.)$ is the step function defined as $\grave{e}(v)=\{0,$ if $v<=0;$ $1,$ if $v>0\}$ and $w(.,.)$ is the scoring function between the two nodes, defined as $$w(a_{ik}, a_{jl}) = \begin{cases} 0, \text{ if } i = j, a_{ik} = a_{jl}, a_{ik} = -D, \text{ or } a_{jl} = -D \\ \text{where } D > 0, \text{ or} \\ \theta[c_{ik,jl} - t_c] \cdot \{\alpha(1 - |s_{ik} - s_{jl}|) + (1 - \alpha)c_{ik,jl}\} \text{ otherwise;} \end{cases}$$

c) finding the best alignment to predict nodes of putative pathways $PPW_j$, $1<=j<=\max n_i$ with the top n best scores.

5. The system of claim 3, wherein the central processing unit runs the constrained clustering algorithm further comprising:
   a) assigning a distance between a protein in a query pathway and each protein in the database;
   b) merging at each round the protein in the query pathway and the protein in the database with the closest distance into a cluster until user-set threshold is met; and
   c) computing mean linkage between two clusters using $$d(c_1, c_2) = \left\{ \frac{1}{n_1 + n_2} \sum_{i \in c_1} \sum_{j \in c_2} d_{ij}^p \right\}^{1/p}$$

where $n_1$ is the size of $c_1$ and $n_2$ is the size of $c_2$ and the distance between the two clusters is a weighted average of the distance between two proteins i and j and a function or similarity to query protein ($s_i=S_{iq(i)}$, $s_j=S_{jq(j)}$) where q(i) is the query protein homologous to database protein i and protein-protein association ($a_{ij}$) and $d_{ij}=\alpha(1-\alpha_{ij})+(1-\alpha)|s_i-s_j|$.

6. The system of claim 1, wherein the central processing unit is further programmed to perform one or more analyses selected from protein sequence analysis, protein interactions analysis, protein-protein association analysis, protein pathway analysis, gene expression analysis, pathway annotation analysis, pathway edit analysis, pathway expression analysis, tissue expression analysis, subtractive hybridization analysis, electronic northern analysis, and commonality analysis.

7. The system of claim 6, wherein protein interactions analysis between a query pathway and each pathway in the database produces a coefficient of similarity to interrelate each mode of the query pathway and a mode of the most closely related protein pathway.

8. The system of claim 1, which each pathway in the database further comprises at least two nodes connected by a mode.

9. The system of claim 8 wherein the central processing unit is further programmed to compare at least two pathways using scores calculated from sequence identity, motif or structural homologies that interrelate nodes and employing coefficients of similarity calculated or selected from gene expression data, a promoter similarity matrix, a protein-protein association matrix and a similarities among protein interactions matrix (SCIM matrix) that interrelate modes of the pathways.

10. The system of claim 1, wherein the central processing unit is further programmed to perform pairwise comparison of at least two pathways or their components selected from node-only, mode-only, and node-and-mode comparison and wherein the node-only comparison is further selected from protein only, non-protein only, and protein and non-protein nodes.

11. The system of claim 10, wherein node-and-mode comparison predicts new homologous or orthologous pathways by comparing node by using an optimization algorithm for dynamic programming or a constrained clustering algorithm or standard methods and modes by generating a SCIM matrix containing coefficients of similarity.

12. A process for analyzing or predicting novel homologous or orthologous pathways comprising:
   a) submitting a query pathway and protein sequences to the system of claim 1;
   b) organizing the pathway and sequences using SLIPR;
   c) comparing each sequence of the query pathway with each sequence in the pathways database using an algorithm for constrained clustering or an optimization algorithm for dynamic programming and standard methods of protein comparison to calculate sequence identity scores;
   d) using a SCIM matrix derived from protein interactions protein-protein association analysis to compare coefficients of similarity for each interaction of the query pathway and each interaction in a pathway in the pathways database;
   e) calculating an overall-similarity score (OS-score) based on sequence identity scores and coefficients of similarity for each pathway; and
   f) retrieving pathways meeting a user-specified threshold for OS-score, thereby analyzing or predicting novel homologous or orthologous pathways.

13. The process of claim 12, wherein the predicted orthologous pathway further comprises orthologous proteins with the highest sequence identity to the proteins in the query pathway and protein interactions inherited from the query pathway.

* * * * *